(12) United States Patent  
Kawamura

(10) Patent No.: US 8,222,637 B2
(45) Date of Patent: Jul. 17, 2012

(54) BENZOCHRYSENE DERIVATIVE AND ORGANIC ELECTROLUMINESCENCE DEVICE USING THE SAME

(75) Inventor: Masahiro Kawamura, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 194 days.

(21) Appl. No.: 12/743,173

(22) PCT Filed: Nov. 10, 2008

(86) PCT No.: PCT/JP2008/070430
§ 371 (c)(1),
(2), (4) Date: Aug. 20, 2010

(87) PCT Pub. No.: WO2009/063833
PCT Pub. Date: May 22, 2009

(65) Prior Publication Data
US 2010/0320451 A1    Dec. 23, 2010

(30) Foreign Application Priority Data
Nov. 15, 2007    (JP) .................................. 2007-297151

(51) Int. Cl.
*H01L 35/24* (2006.01)
(52) U.S. Cl. .................................. 257/40; 257/E51.001
(58) Field of Classification Search .................... 257/40, 257/E51.001
See application file for complete search history.

(56) References Cited

U.S. PATENT DOCUMENTS
5,935,721 A    8/1999    Shi et al.
7,183,010 B2  2/2007    Jarikov
2008/0224603 A1  9/2008  Hashimoto et al.

FOREIGN PATENT DOCUMENTS
JP    2002-231450 A    8/2002
JP    2003-347058 A    12/2003
(Continued)

OTHER PUBLICATIONS

S. Kumar, "A Convenient and General Synthesis of Cata- and Peri-Condensed Polycyclic Aromatic Hydrocarbons with a Fjord-Region," Synthesis 2001, No. 6, pp. 841-844.

(Continued)

*Primary Examiner* — Anthony Ho
(74) *Attorney, Agent, or Firm* — Foley & Lardner LLP

(57) ABSTRACT

A fused aromatic ring derivative shown by the following formula (1):

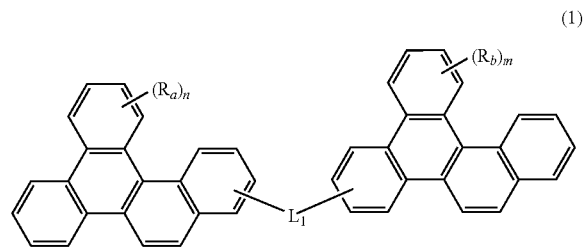

wherein $R_a$ and $R_b$ are independently a hydrogen atom or a substituent, m and n are independently an integer of 1 to 13, and when m and n are two or more, $R_a$s and $R_b$s may be independently the same or different, and $L_1$ is a single bond or a substituted or unsubstituted divalent linking group, provided that the fused aromatic ring derivative shown by the formula (1) does not have an anthracene ring.

12 Claims, 1 Drawing Sheet

FOREIGN PATENT DOCUMENTS

| | | |
|---|---|---|
| JP | 2005-041843 A | 2/2005 |
| JP | 2006-052323 A | 2/2006 |
| JP | 2006-052324 A | 2/2006 |
| JP | 2008-255099 A | 10/2008 |
| WO | WO 2007/126112 A | 11/2007 |

OTHER PUBLICATIONS

T. Yao et al., "Synthesis of Polycyclic Aromatics and Heteroaromatics via Electrophilic Cyclization," Journal Org. Chem., 2005, vol. 70, No. 9, pp. 3511-3517.

A. H. A. Tinnemans et al., "Photodehydrocyclizations in Stilbene-Like Compounds. Rearrangement in Photocyclization of 4,5-Diphenyltriphenylene and 4,5-Diphenylphenanthrene," Journal of the American Chemical Society, 96:14, Jul. 10, 1974, pp. 4617-4622.

H. H. Sellger et al., "Chemical Production of Excited States. Chemiluminescence of Carcinogenic Hydrocarbons Accompanying Their Metabolic Hydroxylation and a Proposal for Common Active Site Geometries for Hydroxylation," The Journal of Physical Chemistry, vol. 80, No. 20, 1976, pp. 2296-2306.

International Search Report mailed Dec. 2, 2008 received in PCT/JP2008/070430.

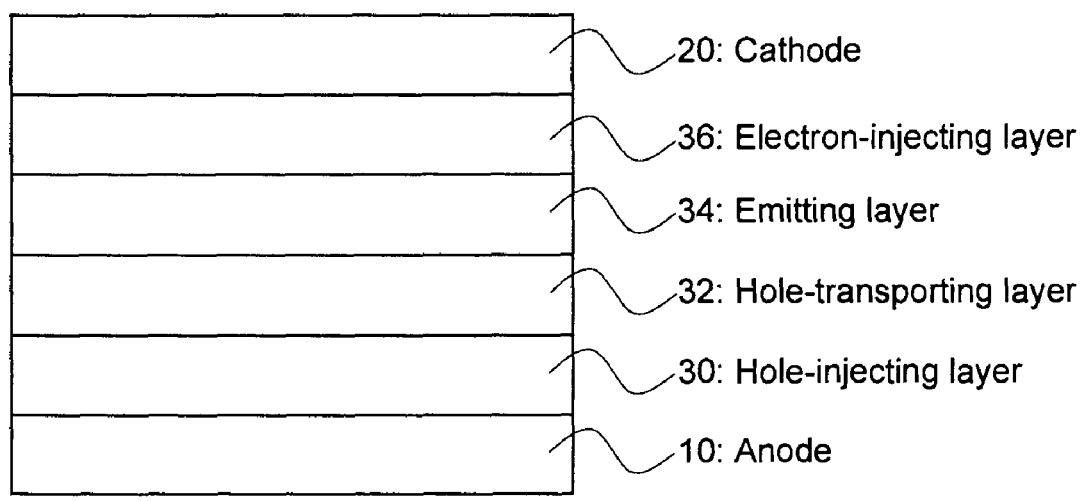

BENZOCHRYSENE DERIVATIVE AND ORGANIC ELECTROLUMINESCENCE DEVICE USING THE SAME

The invention relates to a novel fused aromatic ring derivative (benzochrysene derivative) which is useful as a material for an organic electroluminescence device, and an organic electroluminescence device using the same.

An organic electroluminescence device (hereinafter the term "electroluminescence" is often abbreviated as "EL") is a self-emission device utilizing the principle that an emitting material emits light by the recombination energy of holes injected from an anode and electrons injected from a cathode when an electric field is impressed.

An organic EL device has made a remarkable progress. In addition, since an organic EL device has characteristics such as low voltage driving, high luminance, variety in emission wavelength, high response and capability of fabricating a thin and lightweight emitting device, its application to a wide range of fields is expected.

Emission materials used in an organic EL device have conventionally been studied actively since they influence largely the color of light emitted by a device or on emission life.

As the emission material, a chelate complex such as tris(8-quinolinolato)aluminum complex, a coumarin derivative, a tetraphenylbutadiene derivative, a bisstyrylarylene derivative and an oxadiazole derivative are known. By using such emission materials, emission in a visible range from blue to red can be obtained.

Use of a phosphorescent compound as an emission material for utilizing triplet energy for emission has been studied. For example, it is known that an organic EL device using an iridium complex as an emission material exhibits a high luminous efficiency.

An organic EL device using polyphenylene vinylene (PPV) as a conjugated polymer is known. In this device, PPV is applied and formed into a single film and this device is confirmed to emit light.

Patent Document 1 discloses an organic EL device using a layer containing 9,10-di-(2-naphthyl)anthracene derivative as an organic layer.

Patent Document 1: U.S. Pat. No. 5,935,721

An object of the invention is to provide an organic material which is suitable for use as a material of an organic EL device.

DISCLOSURE OF THE INVENTION

The inventor noticed a benzochrysene derivative as a material for an organic EL device and made intensive studies. As a result, the inventor has found that a benzochrysene derivative having a specific structure is effective for prolonging the lifetime, increasing the efficiency and lowering the voltage of an organic EL device. The invention has been made on this finding.

According to the invention, the following fused aromatic ring derivative or the like can be provided.

1. A fused aromatic ring derivative shown by the following formula (1):

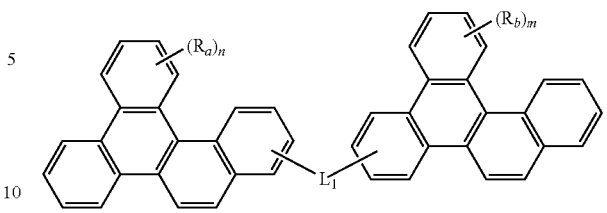

(1)

wherein $R_a$ and $R_b$ are independently a hydrogen atom or a substituent, m and n are independently an integer of 1 to 13, and when m and n are two or more, $R_a$s and $R_b$s may be independently the same or different, and $L_1$ is a single bond or a substituted or unsubstituted divalent linking group, provided that the fused aromatic ring derivative shown by the formula (1) does not have an anthracene ring.

2. The fused aromatic ring derivative according to 1 shown by the following formula (2):

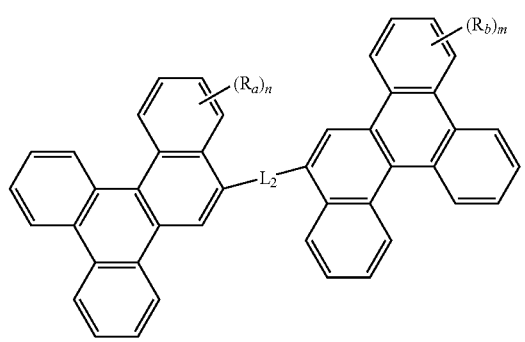

(2)

wherein $R_a$ and $R_b$ are independently a hydrogen atom or a substituent, m and n are independently an integer of 1 to 13, and when m and n are two or more, $R_a$s and $R_b$s may be independently the same or different, and $L_2$ is a single bond or a substituted or unsubstituted divalent linking group, provided that the fused aromatic ring derivative shown in the formula (2) does not have an anthracene ring.

3. The fused aromatic ring derivative according to 1 or 2, wherein $L_1$ or $L_2$ is a substituted or unsubstituted arylene group having 6 to 50 carbon atoms that form a ring (hereinafter abbreviated as the "ring carbon atoms").

4. A material for an organic electroluminescence device comprising the fused aromatic ring derivative according to any one of 1 to 3.

5. The material for an organic electroluminescence device according to 4, which is an emitting material.

6. An organic electroluminescence device comprising:
an anode, a cathode, and
one or more organic thin film layers comprising an emitting later between the anode and the cathode,
wherein at least one of the organic thin film layers comprises the compound according to any one of 1 to 3.

7. The organic electroluminescence device according to 6, wherein the emitting layer comprises the fused aromatic ring derivative.

8. The organic electroluminescence device according to 7, wherein the emitting layer comprises the fused aromatic ring derivative as a host material.

9. The organic electroluminescence device according to any one of 6 to 8, wherein the emitting layer further comprises at least one of a fluorescent dopant and a phosphorescent dopant.
10. The organic electroluminescence device according to 9, wherein the fluorescent dopent is an arylamine compound.
11. The organic electroluminescence device according to 9, wherein the fluorescent dopent is a styrylamine compound.
12. The organic electroluminescence device according to 9, wherein the phosophorescent dopant is a metal complex compound.

According to the invention, a fused aromatic ring derivative suitable for use as a material for an organic EL device can be obtained. An organic EL device using the fused aromatic ring derivative of the invention has a long life and a high efficiency and is capable of being driven at a low voltage.

BRIEF DESCRIPTION OF THE DRAWINGS

FIG. 1 is a schematic cross-sectional view of an organic EL device according to one embodiment of the invention.

BEST MODE FOR CARRYING OUT THE INVENTION

The fused aromatic ring derivative of the invention will be described below in detail.
The fused aromatic ring derivative of the invention is a compound shown by the following formula (1):

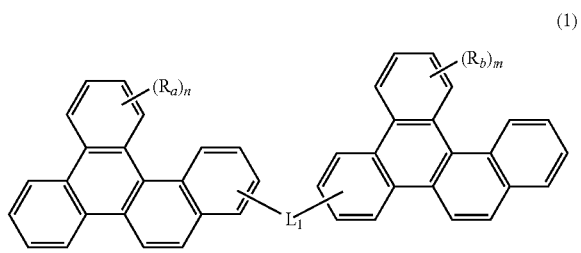

wherein $R_a$ and $R_b$ are independently a hydrogen atom or a substituent, m and n are independently an integer of 1 to 13, and when m and n are two or more, $R_a$s and $R_b$s may be the same or different, and $L_1$ is a single bond or a substituted or unsubstituted divalent linking group, provided that the fused aromatic ring derivative shown by the formula (1) does not have an anthracene ring.

In the formula (1), $L_1$ may be bonded to any of the 14 bonding positions of the benzochrysene ring.

Similarly, $R_a$ and $R_b$ may be bonded to any of the 13 bonding positions except for the bonding position of $L_1$.

Examples of the substituent shown by $R_a$ and $R_b$ include an alkyl group (one having preferably 1 to 20, more preferably 1 to 12 and particularly preferably 1 to 8 carbon atoms, the specific examples of which include methyl, ethyl, isopropyl, t-butyl, n-octyl, n-decyl, n-hexadecyl, cyclopropyl, cyclopentyl and cyclohexyl), an alkenyl group (one having preferably 2 to 20, more preferably 2 to 12 and particularly preferably 2 to 8 carbon atoms, the specific examples of which include vinyl, allyl, 2-butenyl and 3-pentenyl), an alkynyl group (one having preferably 2 to 20, more preferably 2 to 12 and particularly preferably 2 to 8 carbon atoms, the specific examples of which include propynyl and 3-pentynyl), and a substituted or unsubstituted aryl group (one having preferably 6 to 20 and particularly preferably 6 to 14 carbon atoms, the specific examples of which include phenyl, naphthyl, naphthylphenyl, phenylnaphthyl, naphthylnaphthyl, phenanthryl, fluorenyl, provided that an anthracene ring is not contained). Examples of the substituent for the aryl group include an aryl group (one having preferably 6 to 20 and particularly preferably 6 to 14 carbon atoms, the specific examples include phenyl, naphthyl and phenanthryl, provided that an anthracene ring is not contained), a heterocyclic group (one having preferably 1 to 30 and more preferably 1 to 12 carbon atom, the specific examples of which include imidazolyl, pyridyl, quinolyl, furyl, thienyl, piperidyl, morpholino, benzooxazolyl, benzoimidazolyl, benzothiazolyl, carbazolyl, benzofuranyl, dibenzofuranyl, benzothiophenyl and dibenzothiophenyl), a substituted or unsubstituted amino group (one having preferably 0 to 20, more preferably 0 to 12 and particularly preferably 0 to 6 carbon atoms, the specific examples of which include amino, methylamino, dimethylamino, diethylamino, diphenylamino and dibenzylamino), an alkoxy group (one having preferably 1 to 20, more preferably 1 to 12 and particularly preferably 1 to 8 carbon atoms, the specific examples of which include methoxy, ethoxy and buthoxy), an aryloxy group (one having preferably 6 to 20, more preferably 6 to 16 and particularly preferably 6 to 12 carbon atoms, the specific examples of which include phenyloxy and 2-naphthyloxy), an acyl group (one having preferably 1 to 20, more preferably 1 to 16 and particularly preferably 1 to 12 carbon atoms, the specific examples of which include acetyl, benzoyl, formyl and pivaloyl), an alkoxycarbonyl group (one having preferably 2 to 20, more preferably 2 to 16 and particularly preferably 2 to 12 carbon atoms, the specific examples of which include methoxycarbonyl and ethoxycarbonyl), an aryloxycarbonyl group (one having preferably 7 to 20, more preferably 7 to 16 and particularly preferably 7 to 10 carbon atoms, the specific examples of which include phenyloxycarbonyl), an acyloxy group (one having preferably 2 to 20, more preferably 2 to 16 and particularly preferably 2 to 10 carbon atoms, the specific examples of which include acetoxy and benzoyloxy), an acylamino group (one having preferably 2 to 20, more preferably 2 to 16 and particularly preferably 2 to 10 carbon atoms, the specific examples of which include acetylamino and benzoylamino), an alkoxycarbonylamino group (one having preferably 2 to 20, more preferably 2 to 16 and particularly preferably 2 to 12 carbon atoms, the specific examples of which include methoxycarbonylamino), an aryloxycarbonylamino group (one having preferably 7 to 20, more preferably 7 to 16 and particularly preferably 7 to 12 carbon atoms, the specific examples of which include phenylcarbonylamino), a substituted or unsubstituted sulfonylamino group (one having preferably 1 to 20, more preferably 1 to 16 and particularly preferably 1 to 12 carbon atoms, the specific examples of which include methanesulfonylamino and benzenesulfonylamino), a substituted or unsubstituted sulfamoyl group (one having preferably 0 to 20, more preferably 0 to 16 and particularly preferably 0 to 12 carbon atoms, the specific examples of which include sulfamoyl, methylsulfamoyl, dimethylsulfamoyl and phenylsulfamoyl), a substituted or unsubstituted carbamoyl group (one having preferably 1 to 20, more preferably 1 to 16 and particularly preferably 1 to 12 carbon atoms, the specific examples of which include carbamoyl, methylcarbamoyl, diethylcarbamoyl and phenylcarbamoyl), an alkylthio group (one having preferably 1 to 20, more preferably 1 to 16 and particularly preferably 1 to 12 carbon atoms, the specific examples of which include methylthio and ethylthio), an arylthio group (one having preferably 6 to 20, more preferably 6 to 16 and particularly preferably 6 to 12 carbon atoms, the specific examples of which include phenylthio), a substituted or unsubstituted sulfonyl group (one having preferably 1 to 20, more preferably 1 to 16 and particularly preferably 1 to 12 carbon atoms, the specific examples of which include mesyl and tosyl), a substituted or unsubstituted sulfinyl group (one having preferably 1 to 20, more preferably 1 to 16 and particularly preferably 1 to 12 carbon atoms, the specific examples of which include methanesulfinyl and benezenesulfinyl), a substituted or unsubstituted ureido group (one having preferably 1 to 20, more preferably 1 to 16 and particularly preferably 1 to 12 carbon atoms, the specific examples include ureido, methylureido and phenylureido), a substituted or unsubstituted phosphoric amide group (one having preferably 1 to 20, more preferably 1 to 16 and particularly preferably 1 to 12 carbon atoms, the specific examples of which include diethylphosphoric amide and phenylphosphoric amide), a hydroxy group, a mercapto group, a halogen atom (for example, a fluorine atom, a chlorine atom, a bromine atom and an iodine atom), a cyano group, a sulfo group, a carboxyl group, a nitro group, a hydroxamic acid group, a sulfino group, a hydrazino group, an imino group, a heterocyclic group (one having preferably 1 to 30 and more preferably 1 to 12 carbon atoms and containing, as the hetero atom, a nitrogen atom, an oxygen atom and a sulfur atom, for example, the specific examples of which include imidazolyl, pyridyl, quinolyl, furyl, thienyl, piperidyl, morpholino, benzoxazolyl, benzimidazoyl, benzothiazolyl, carbazolyl, benzofuranyl, dibenzofuranyl, benzothiophenyl and dibenzothiophenyl), and a silyl group (one having preferably 3 to 40, more preferably 3 to 30 and particularly preferably 3 to 24 carbon atoms, the specific examples of which include trimethylsilyl and triphenylsilyl). These substituents may be further substituted. If there are two or more substituents, these substituents may be the same or different.

Of these, an alkyl group, an alkenyl group, an aryl group, an arylamino group, a carbazolyl group, a carbazolylaryl group, a dibenzofuranyl aryl group and a dibenzothiophenyl aryl group are preferable.

As the substituted or unsubstituted divalent linking group shown by $L_1$, for example, a substituted or unsubstituted alkylene group, a substituted or unsubstituted arylene group having 6 to 50 ring carbon atoms and a substituted or unsubstituted heterocyclic group having 5 to 50 atoms that form a ring (hereinafter referred to as the "ring atoms") can be given.

As examples of the substituted or unsubstituted alkylene group, a divalent group obtained by removing one hydrogen atom from the following alkyl groups having 1 to 20 carbon atoms can be given:

Methyl, ethyl, isopropyl, t-butyl, n-octyl, n-decyl, n-hexadecyl, cyclopropyl, cyclopentyl, cyclohexyl.

As the substituent of these, the above-mentioned alkyl group, or the aryl group or the heterocyclic group given later can be given, for example.

As examples of the substituted or unsubstituted arylene group having 6 to 50 ring carbon atoms, a divalent group obtained by removing one hydrogen atom from the following aryl groups can be given:

A phenyl group, 1-naphthyl group, 2-naphthyl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4'-methylbiphenylyl group, 4"-t-butyl-p-terphenyl-4-yl group, triphenylenyl group, benzanthranyl group, 1-chrysenyl group, 2-chrysenyl group, 6-chrysenyl group, phenyl-1-naphthyl group, phenyl-2-naphthyl group, naphthyl-1-naphthyl group, naphthyl-2-naphthyl group.

As the substituent of these, the above-mentioned alkyl group, or the aryl group or the heterocyclic group given later can be given, for example.

As examples of the substituted or substituted heterocyclic group having 5 to 50 ring atoms, a divalent group obtained by removing one hydrogen atom from the following monovalent heterocyclic ring groups can be given:

Imidazolyl, pyridyl, quinolyl, furyl, thienyl, piperidyl, morpholino, benzooxazolyl, benzoimidazolyl, benzothiazolyl, carbazolyl, benzofuranyl, dibenzofuranyl, benzothiophenyl, dibenzothiophenyl.

As the substituent of these, the alkyl group, the aryl group or the heterocyclic group as mentioned above can be given, for example.

It may be a group obtained by combining two or more of divalent groups such as the arylene group, the heterocyclic group, the single bond, the alkylene group or the like as mentioned above, or a group having a fluorene structure. For example, the following groups can be given.

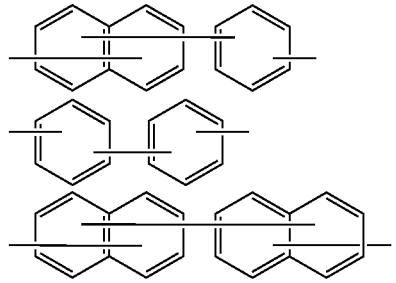

In particular, the following divalent groups are preferable.

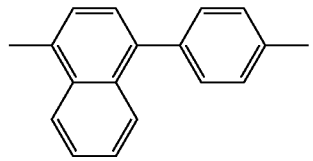

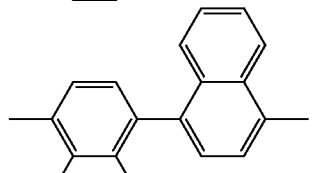

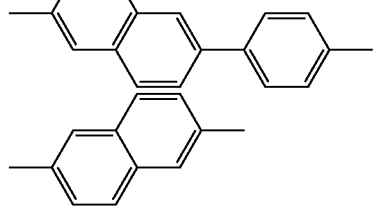

-continued

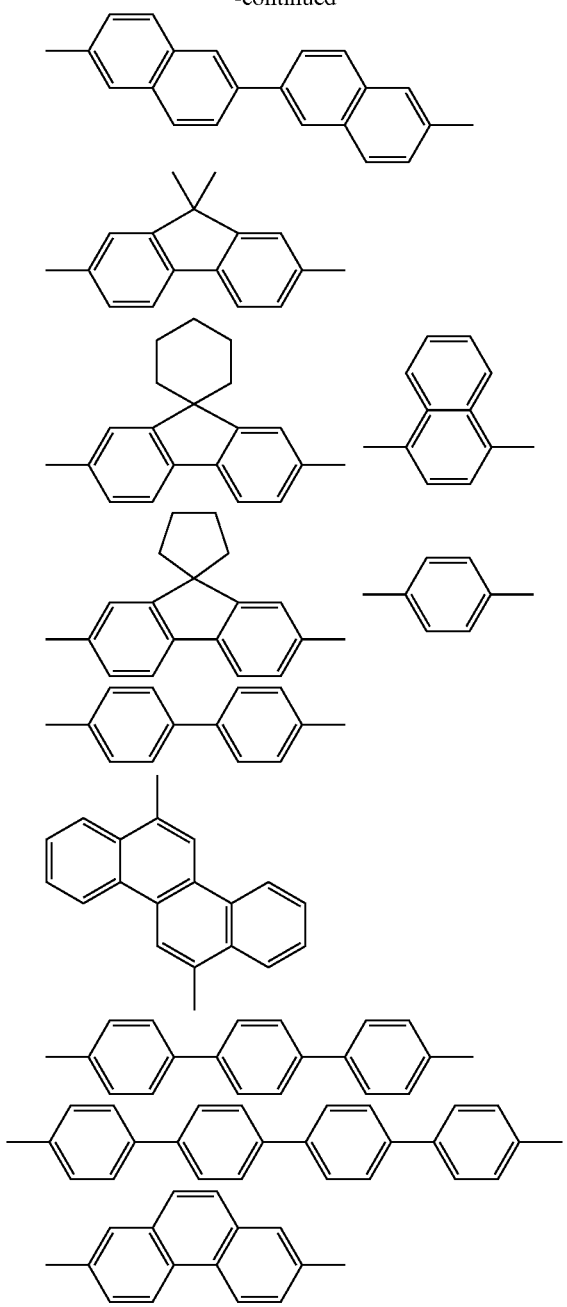

The fused aromatic ring derivative of the invention does not have an anthracene ring. Here, the "does not have an anthracene ring" means that $L_1$ or $L_2$ does not have an anthracenyl group, an anthracenylene group or the like. That is, the fused aromatic ring derivative of the invention does not mean one which has an anthracene skeleton in a fused ring, such as naphthacene and penthacene.

M and n are independently an integer of 1 to 13. In the invention, it is preferred that all of $R_a$ and $R_b$ are hydrogen atoms.

In the fused aromatic ring derivative of the invention, the $10^{th}$ position of the following benzo[g]chrysene has a high reactivity.

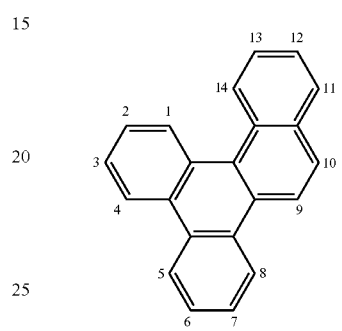

Therefore, the fused aromatic ring derivative of the invention is preferably one shown by the following formula (2), in which a substituent is bonded to the $10^{th}$ position:

(2)

wherein $R_a$, $R_b$, m and n are as defined in the formula (1). $L_2$ is the same group as $L_1$ in the formula (1).

The specific examples of the fused aromatic ring derivative of the invention will be given below.

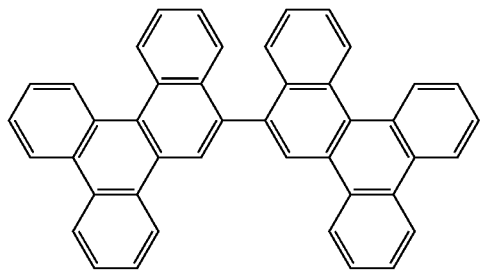 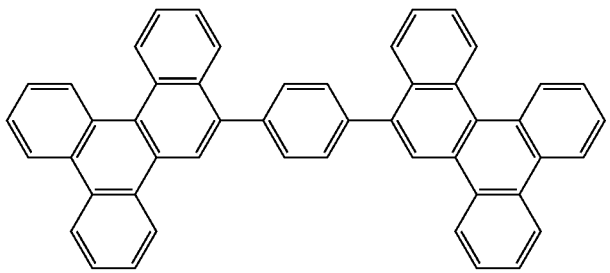

-continued
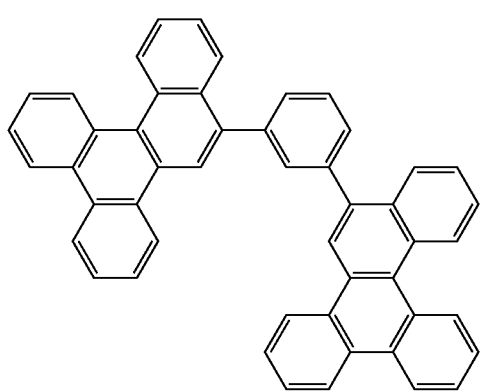
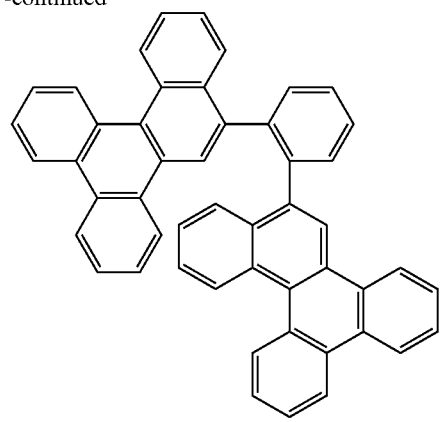
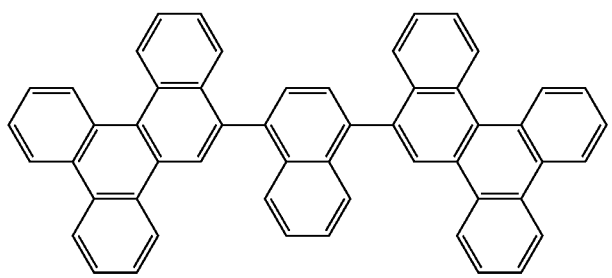
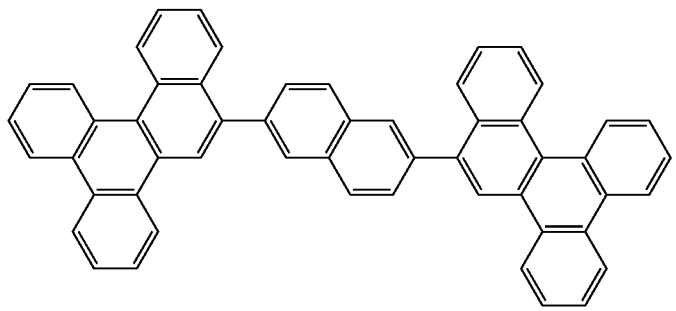
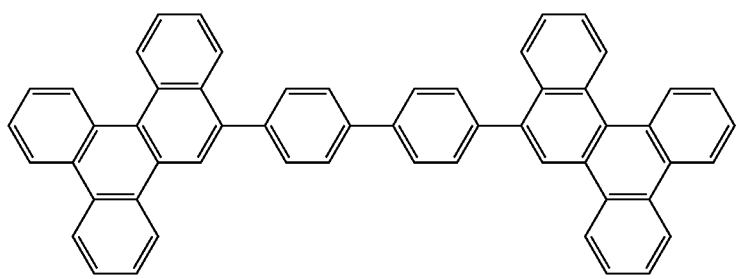
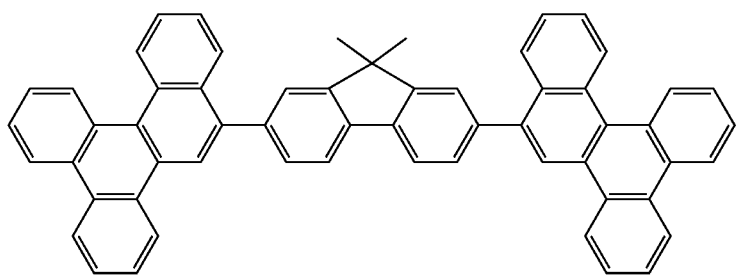

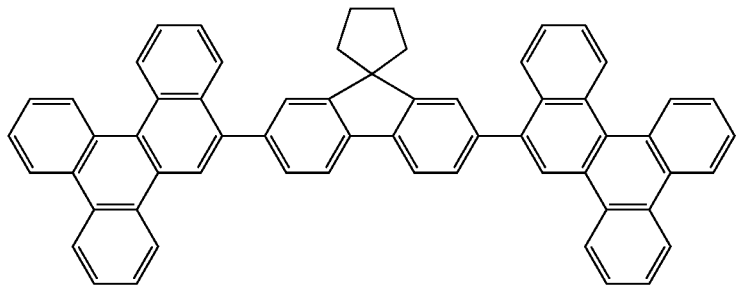

-continued
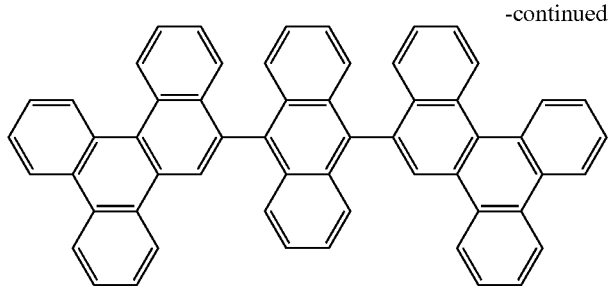
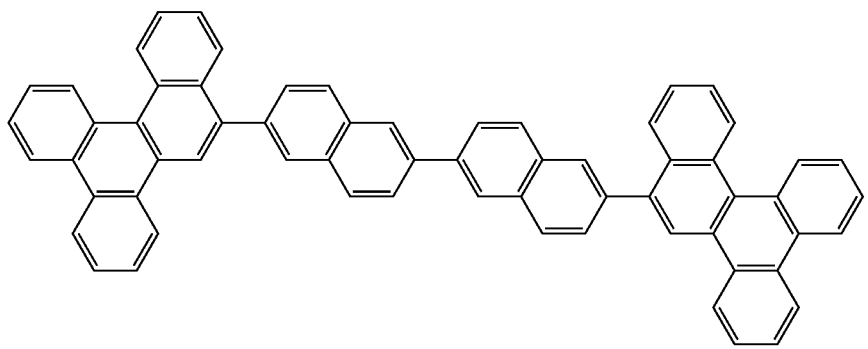
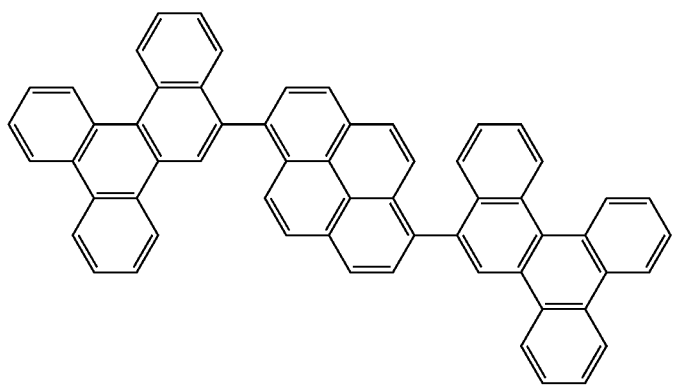
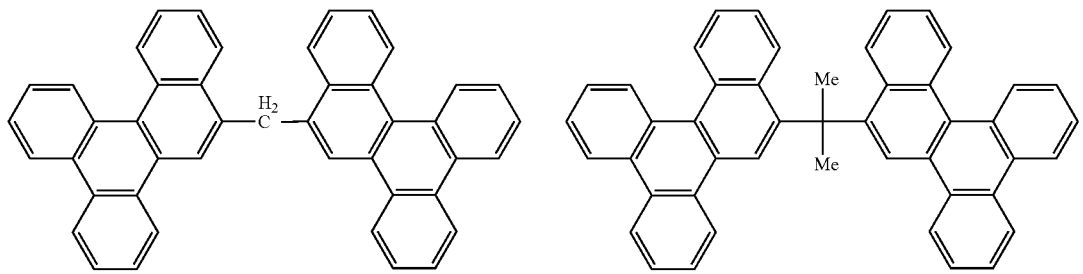
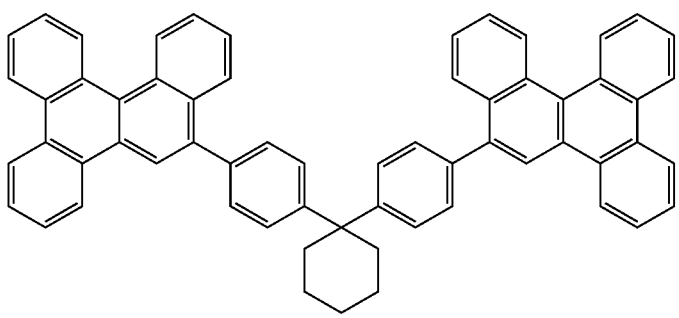

-continued
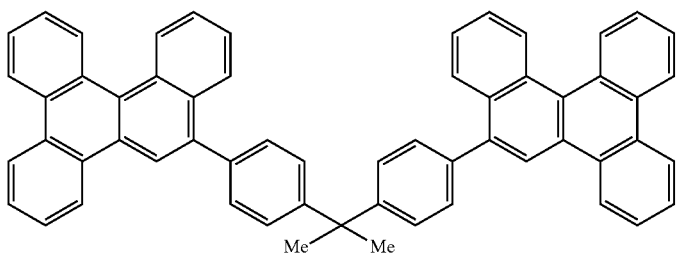
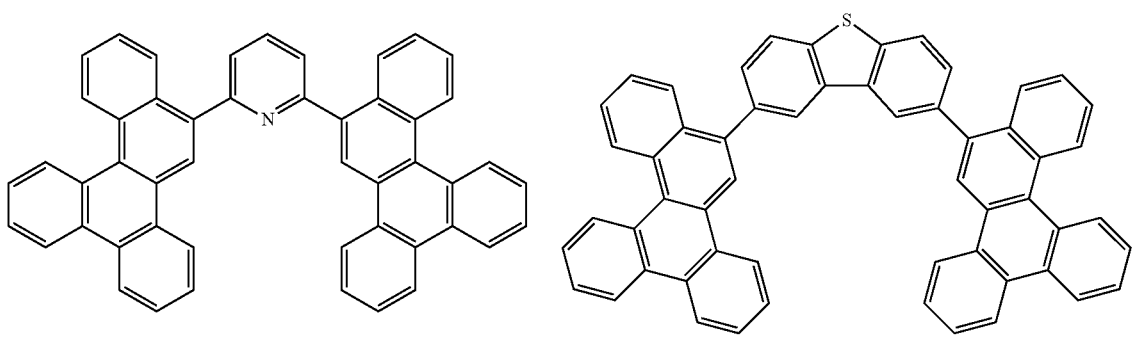
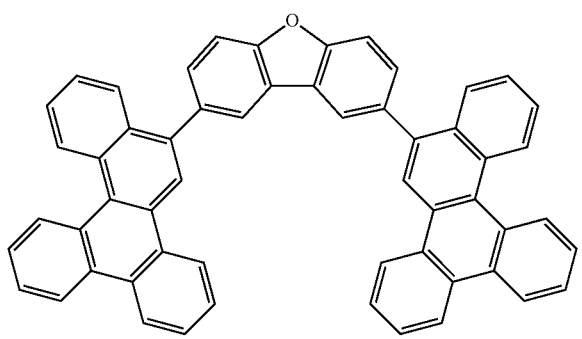
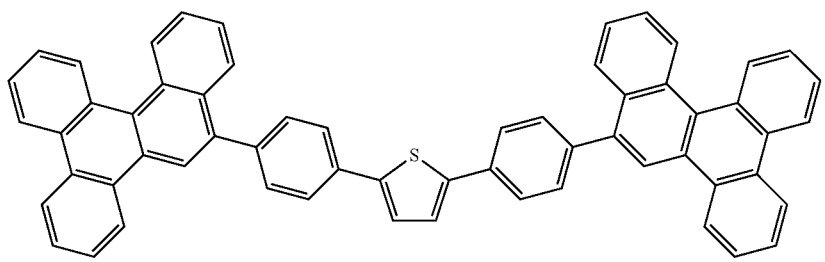
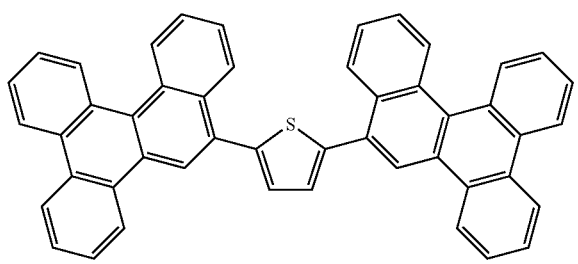

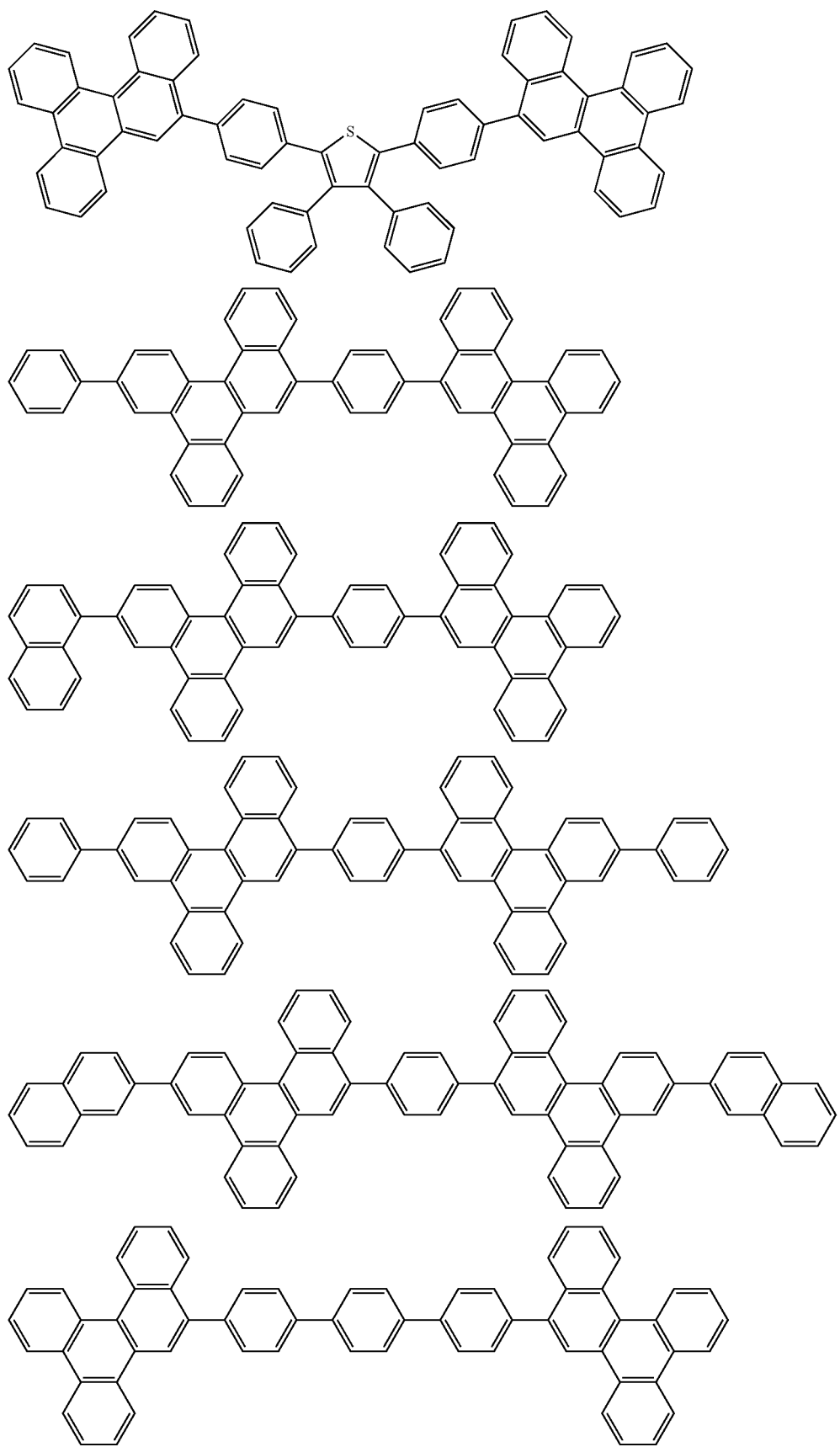

-continued
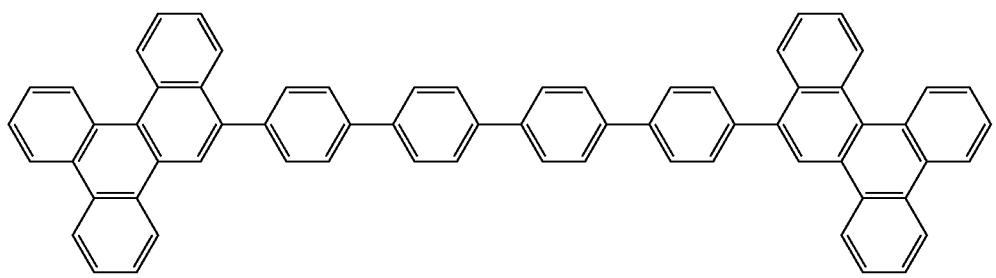
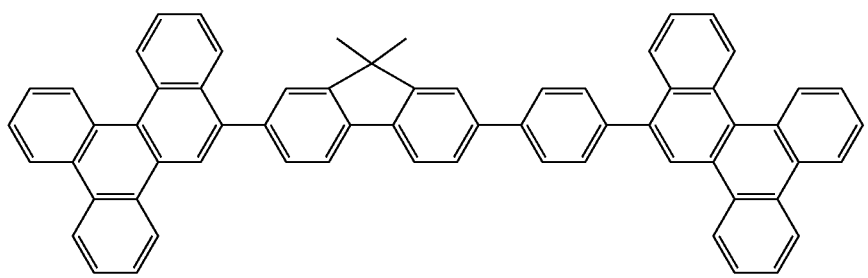
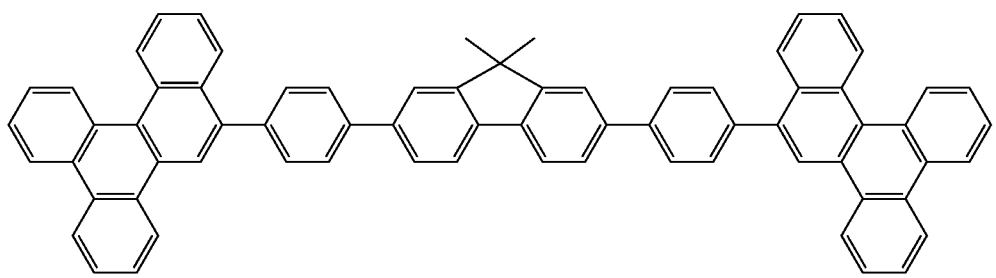
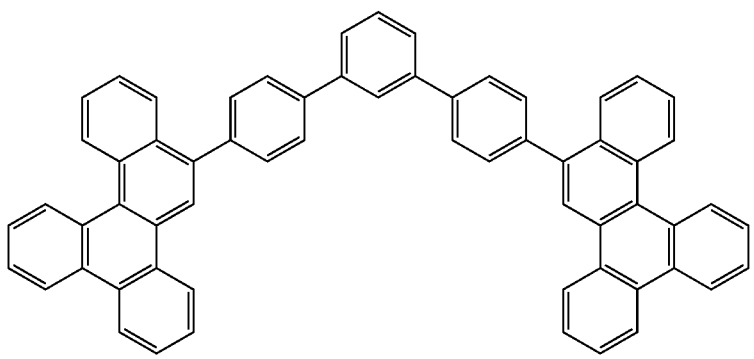
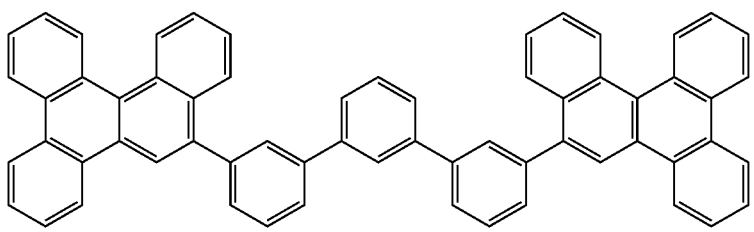

-continued
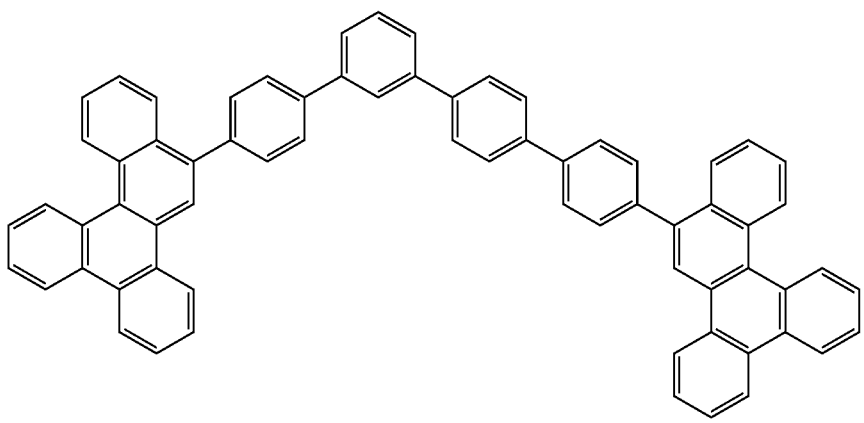
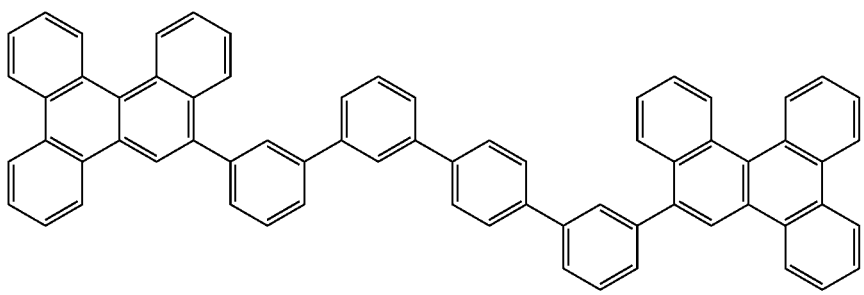
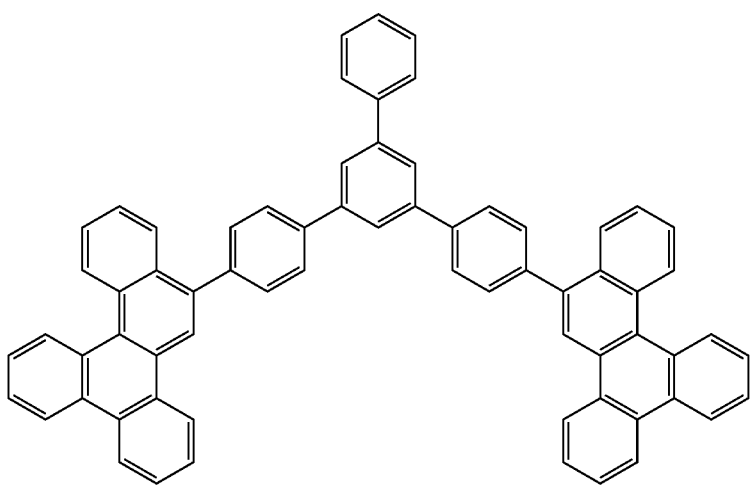

-continued
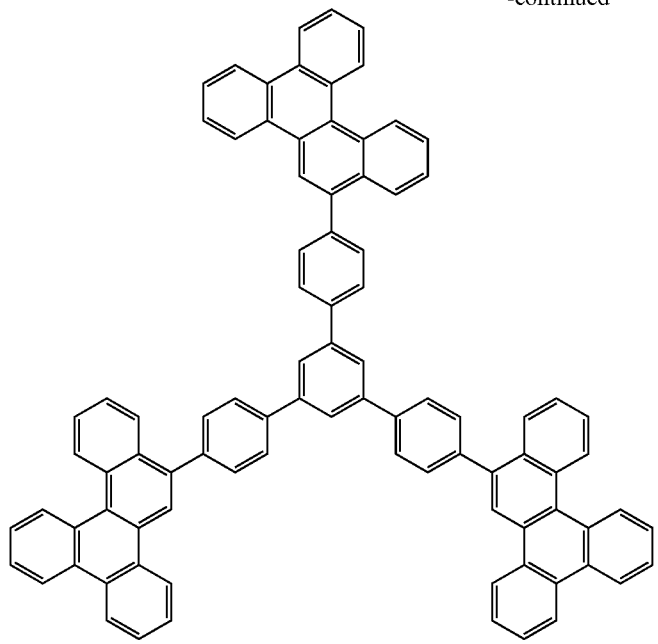
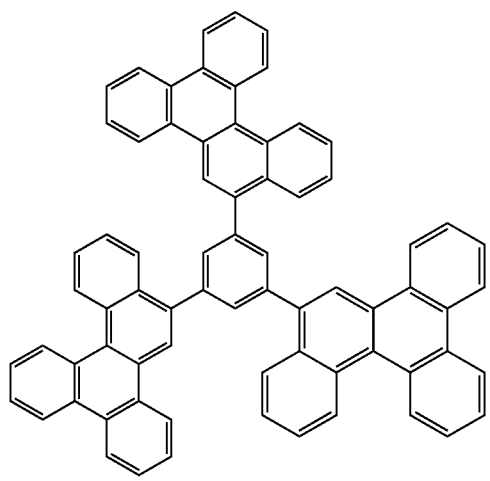
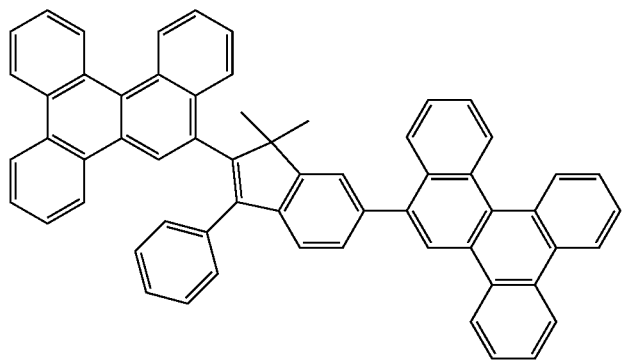

-continued
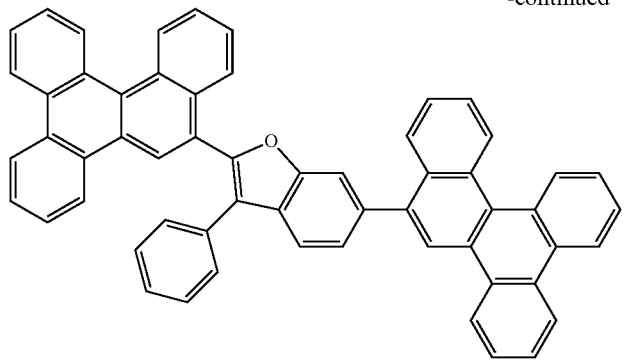
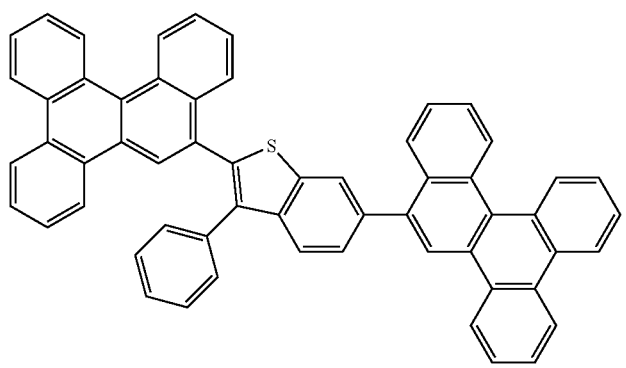
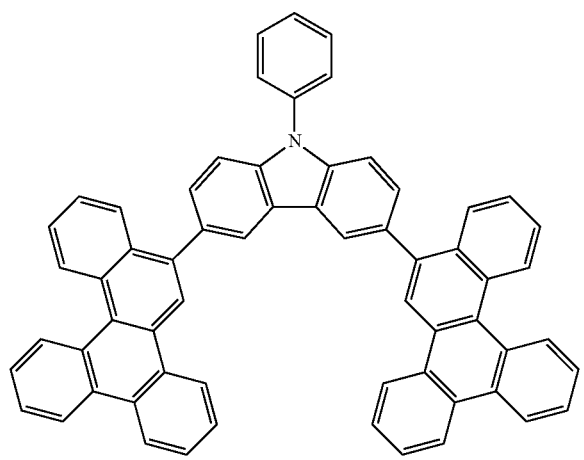
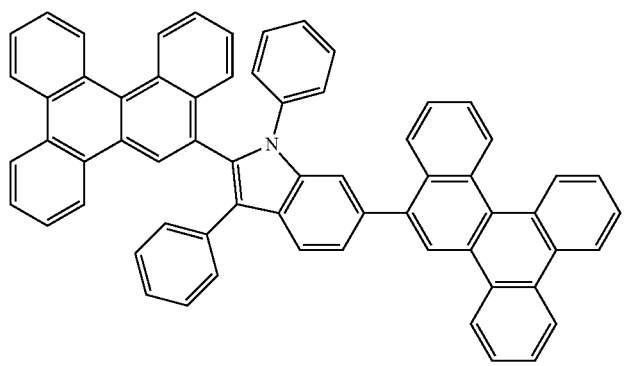

-continued
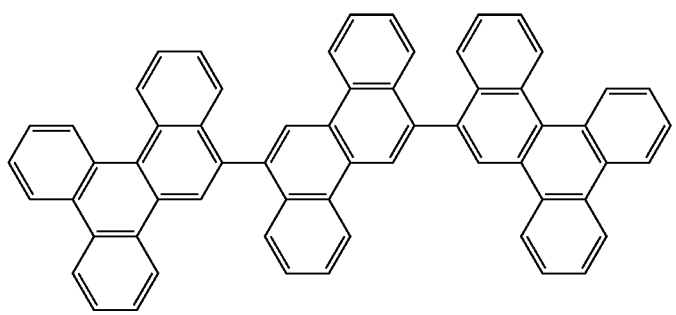
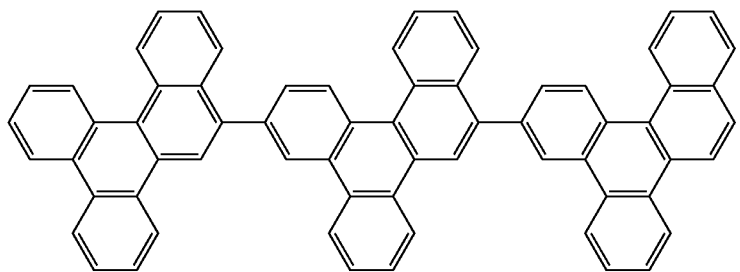
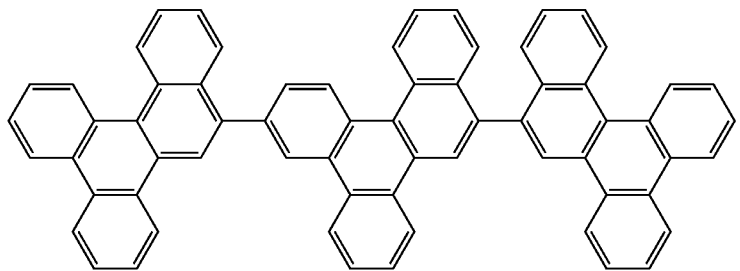
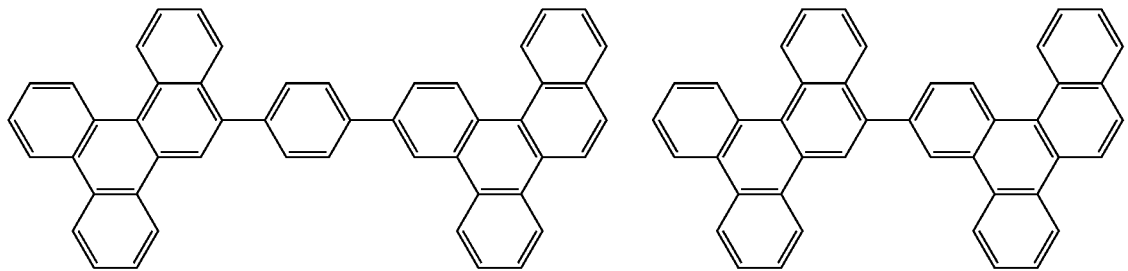
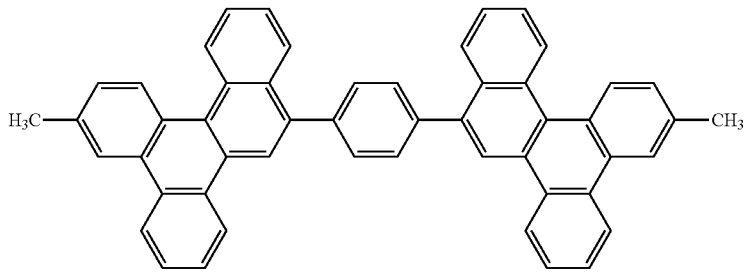
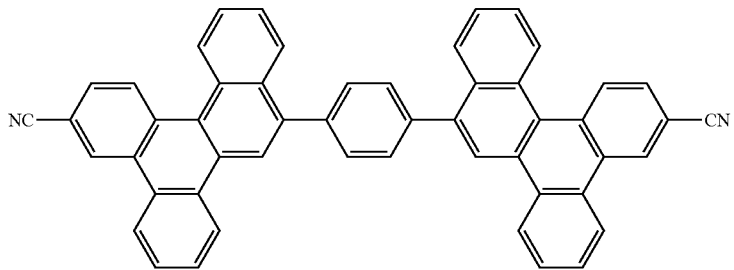

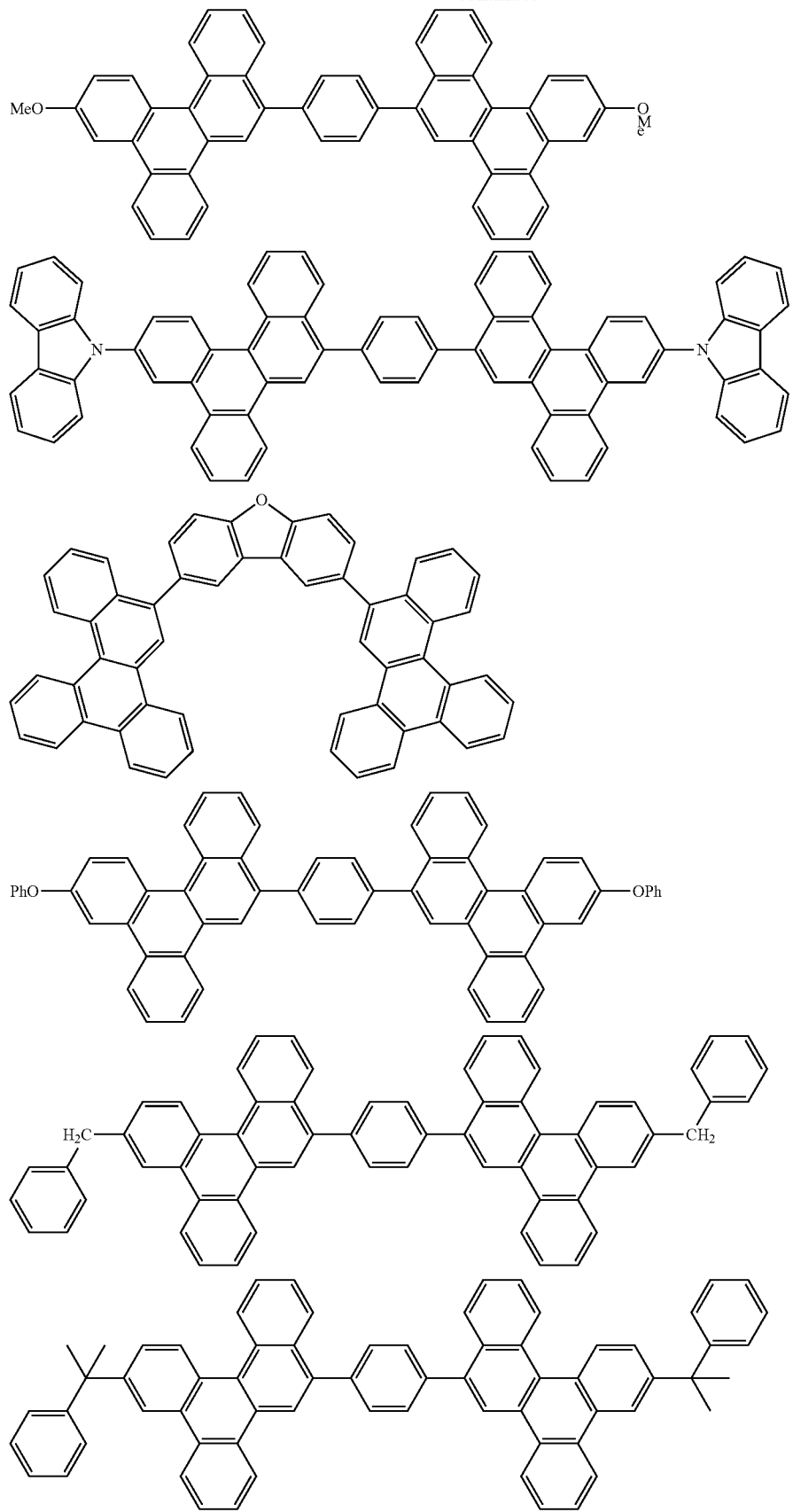

The fused aromatic ring derivative can be synthesized by a method in which a dihalogen compound having the above-mentioned structure $L_1$ is reacted with an intermediate obtained by hydroborating the benzo[g]chrysene synthesized by referring to the following literatures.

[Synthesis 2001, No. 6, 841-844]

[J. Org. Chem. 2005, 70, 3511-3517]

[Journal of the American Chemical Society 96:14 Jul. 10, 1974, 4617-4622]

The fused aromatic ring derivative of the invention can be preferably used as a material for an organic EL device, in particular, as the emitting material thereof.

The organic EL device of the invention comprises an anode, a cathode and one or more organic thin layers comprising an emitting layer between the anode and the cathode, and at least one of the organic thin layers comprise the above-mentioned compound of the invention.

Representative configurations of the organic EL device of the invention can be given below.
(1) Anode/emitting layer/cathode
(2) Anode/hole-injecting layer/emitting layer/cathode
(3) Anode/emitting layer/electron-injecting layer/cathode
(4) Anode/hole-injecting layer/emitting layer/electron-injecting layer/cathode
(5) Anode/organic semiconductor layer/emitting layer/cathode
(6) Anode/organic semiconductor layer/electron-barrier layer/emitting layer/cathode
(7) Anode/organic semiconductor layer/emitting layer/adhesion-improving layer/cathode
(8) Anode/hole-injecting layer/hole-transporting layer/emitting layer/electron-injecting layer/cathode
(9) Anode/insulating layer/emitting layer/insulating layer/cathode
(10) Anode/inorganic semiconductor layer/insulating layer/emitting layer/insulating layer/cathode
(11) Anode/organic semiconductor layer/insulating layer/emitting layer/insulating layer/cathode
(12) Anode/insulating layer/hole-injecting layer/hole-transporting layer/emitting layer/insulating layer/cathode
(13) Anode/insulating layer/hole-injecting layer/hole-transporting layer/emitting layer/electron-injecting layer/cathode The representative examples of the configuration of the organic EL device of the invention are, however, not limited to the above. Of these, the configuration (8) is preferable.

The configuration (8) is shown in FIG. 1. This organic EL device comprises an anode 10, a cathode 20, and a hole-injecting layer 30, a hole-transporting layer 32, an emitting layer 34 and an electron-injecting layer 36 between the anode and the cathode. The hole-injecting layer 30, the hole-transporting layer 32, the emitting layer 34 and the electron-injecting layer 36 correspond to the plurality of organic thin film layers. At least one of these organic thin film layers 30, 32, 34 and 36 comprises the compound of the invention.

In the organic EL device of the invention, although the compound of the invention may be used in any of the above-mentioned organic thin film layers, it is preferred that the compound of the invention be used in the emitting layer. In each of the organic thin film layers, the compound of the invention may be used either singly or in mixture with other compounds. In the device of the invention, it is preferred that the emitting layer contain the compound of the invention as a host material and contain at least one of a fluorescent dopant and a phosphorescent dopant.

In the invention, it is preferred that the emitting layer consist essentially of the compound of the invention and the above-mentioned dopant.

The content of the compound of the invention in the organic thin film layers is preferably 30 to 100 mol %.

Each member of the organic EL device will be explained below.

The organic EL device is normally formed on a substrate. The substrate supports the organic EL device. It is preferable to use a smooth substrate. If light is outcoupled through the substrate, it is preferred that the substrate be a transparent substrate with a transmission to visible rays with a wavelength of 400 to 700 nm of 50% or more.

As such tranparent substrate, a glass plate, a synthetic resin plate or the like are preferably used. Examples of the glass plate include plates of soda-lime glass, barium/strontium-containing glass, lead glass, aluminosilicate glass, borosilicate glass, barium borosilicate glass, quartz, or the like. Examples of the synthetic resin plates include plates of a polycarbonate resin, an acrylic resin, a polyethylene terephthalate resin, a polyether sulfide resin, a polysulfone resin, or the like.

It is effective that the anode injects holes to the hole-injecting layer, the hole-transporting layer or the emitting layer and has a work function of 4.5 eV or more. Specific examples of the anode material include indium tin oxide (ITO), a mixture of indium oxide and zinc oxide, a mixture of ITO and cerium oxide (ITCO), a mixture of the mixture of indium oxide, and zinc oxide and cerium oxide (IZCO), a mixture of indium oxide and cerium oxide (ICO), a mixture of zinc oxide and aluminum oxide (AZO), tin oxide (NESA), gold, silver, platinum and copper.

The anode can be formed from these electrode materials by a vapor deposition method, a sputtering method or the like.

In the case where emission from the emitting layer is outcoupled through the anode, the transmittance of the anode to the emission is preferably more than 10%. The sheet resistance of the anode is preferably several hundred $\Omega/\square$ or less. The film thickness of the anode, which varies depending upon the material thereof, is usually from 10 nm to 1 μm, preferably from 10 to 200 nm.

The emitting layer has the following functions.
(i) Injection function: function of allowing injection of holes from the anode or hole-injecting layer and injection of electrons from the cathode or electron-injecting layer upon application of an electric field
(ii) Transporting function: function of moving injected carriers (electrons and holes) due to the force of an electric field
(iii) Emission function: function of recombining electons and holes to emit light As the method of forming the emitting layer, a known method such as deposition, spin coating, or an LB method may be applied. It is preferable that the emitting layer be a molecular deposition film. The molecular deposition film is a film formed by deposition of a material compound in a gas phase, or by solidification of a material compound in the form of a solution or in a liquid phase. The molecular deposition film can be usually distinguished from a thin film (molecular accumulation film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by spin coating or the like.

Specific examples of the emitting material which can be used in the emitting layer include for example, anthracene, naphthalene, phenanthrene, pyrene, tetracene, coronene, chrysene, fluorescein, perylene, phthaloperylene, naphthaloperylene, perynone, phthaloperynone, naphthaloperynone, diphenyl butadiene, tetraphenyl butadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxinoid compounds, quinacridone, rubrene, and derivatives thereof, and fluorescent pigments, but are not limited to these.

Specific examples of the host material which can be used in the emitting layer include compounds shown by the following formulas (i) to (ix):

Asymmetrical anthracene represented by the following formula (i):

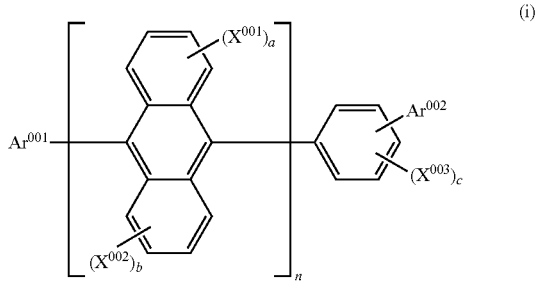

(i)

wherein $Ar^{001}$ is a substituted or unsubstituted fused aromatic group having 10 to 50 ring carbon atoms, $Ar^{002}$ is a substituted or unsubstituted aromatic group having 6 to 50 ring carbon atoms, $X^{001}$ to $X^{003}$ are independently a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group and a hydroxy group, a, b and c are each an integer of 0 to 4.

n is an integer of 1 to 3, and when n is two or more, groups in the [ ]s may be the same or different.

Asymmetrical monoanthracene derivatives represented by the following formula (ii):

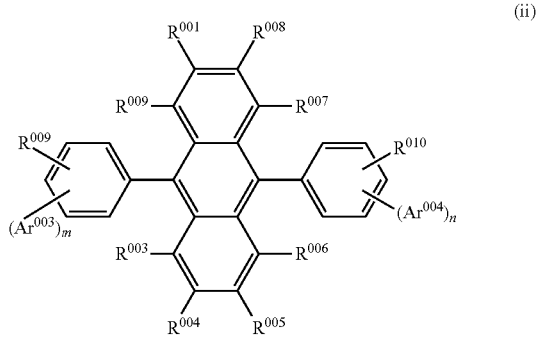

(ii)

wherein $Ar^{003}$ and $Ar^{004}$ are independently are a substituted or unsubstituted aromatic ring group having 6 to 50 ring carbon atoms, m and n are each an integer of 1 to 4, provided that in the case where m=n=1 and $Ar^{003}$ and $Ar^{004}$ are symmetrically bonded to the benzene rings, $Ar^{003}$ and $Ar^{004}$ are not the same, and in the case where m or n is an integer of 2 to 4, m is different from n, $R^{001}$ to $R^{010}$ are independently are a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group.

Asymmetrical pyrene derivatives shown by the following formula (iii):

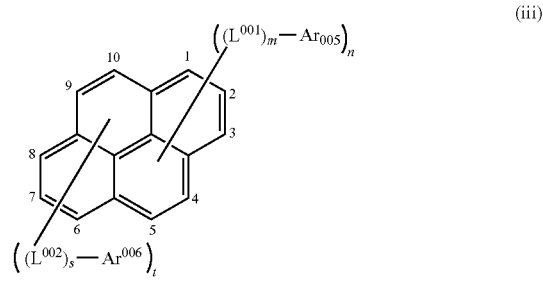

(iii)

wherein $Ar^{005}$ and $Ar^{006}$ are independently an aromatic group having 6 to 50 ring carbon atoms, $L^{001}$ and $L^{002}$ are independently a substituted or unsubstituted phenylene group, a substituted or unsubstituted naphthalenylene group, a substituted or unsubstituted fluolenylene group, or a substituted or unsubstituted dibenzosilolylene group, m is an integer of 0 to 2, n is an integer of 1 to 4, s is an integer of 0 to 2, and t is an integer of 0 to 4, $L^{001}$ or $Ar^{005}$ bonds at any one position of 1 to 5 of the pyrene, and $L^{002}$ or $Ar^{006}$ bonds at any one position of 6 to 10 of the pyrene; provided that when n+t is an even number, $Ar^{006}$, $Ar^{006}$, $L^{001}$ and $L^{002}$ satisfy the following (1) and (2):

(1) $Ar^{006} \neq Ar^{006}$ and/or $L^{001} \neq L^{002}$ where $\neq$ means these substituents are groups having different structures from each other, (2) when $Ar^{005}=Ar^{006}$ and $L^{001}=L^{002}$, (2-1) m$\neq$s and/or n$\neq$t, or (2-2) when m=s and n=t, (2-2-1) when $L^{001}$ and $L^{002}$ or pyrene are independently bonded to different bonding positions of $Ar^{005}$ and $Ar^{006}$, or (2-2-2) when $L^{001}$ and $L^{002}$ or pyrene are bonded to the same position of $Ar^{005}$ and $Ar^{006}$, the positions of the substitution of $L^{001}$ and $L^{002}$ or $Ar^{005}$ and $Ar^{006}$ at pyrene are neither the $1^{st}$ position and the $6^{th}$ position, nor the $2^{nd}$ position and the $7^{th}$ position.

Asymmetrical anthracene shown by the following formula (iv):

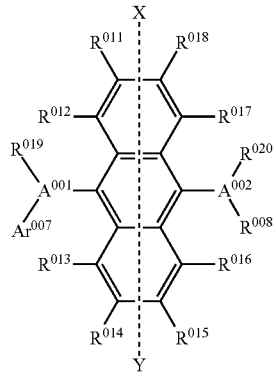

(iv)

wherein $A^{001}$ and $A^{002}$ are independently a substituted or unsubstituted fused aromatic ring group having 10 to 20 ring carbon atoms, $Ar^{007}$ and $Ar^{008}$ are independently a hydrogen atom or a substituted or unsubstituted aromatic ring group having 6 to 50 ring carbon atoms, $R^{011}$ to $R^{020}$ are independently are a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group, and there may be a plurality of $Ar^{007}$, $Ar^{008}$, $R^{019}$ and $R^{020}$, respectively, and adjacent groups thereof may form a saturated or unsaturated ring structure, provided that groups do not symmetrically bond to 9 and 10 positions of the central anthracene with respect to X-Y axis.

Anthracene derivative represented by the following formula (v):

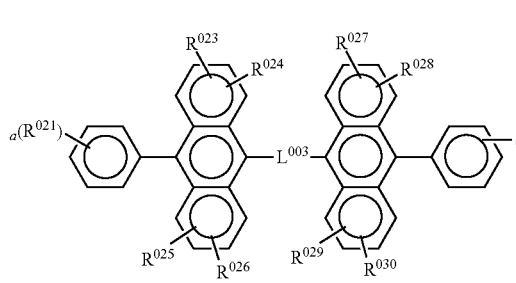

(v)

wherein $R^{021}$ to $R^{030}$ are independently a hydrogen atom, an alkyl group, a cycloalkyl group, a substituted or unsubstituted aryl group, an alkoxy group, an aryloxy group, an alkylamino group, an alkenyl group, an arylamino group or a substituted or unsubstituted heterocyclic group, a and b are independently an integer of 1 to 5, and when they are two or more, $R^{021}$s or $R^{022}$s may be the same or different, $R^{021}$s or $R^{022}$s may be bonded to form a ring, $R^{023}$ and $R^{024}$, $R^{025}$ and $R^{026}$, $R^{027}$ and $R^{028}$, and $R^{029}$ and $R^{030}$ may be bonded to each other to form a ring, and $L^{003}$ is a single bond, —O—, —S—, —N(R)— (R is an alkyl group or a substituted or unsubstituted aryl group), an alkylene group or an arylene group.

Anthracene derivative shown by the following formula (vi):

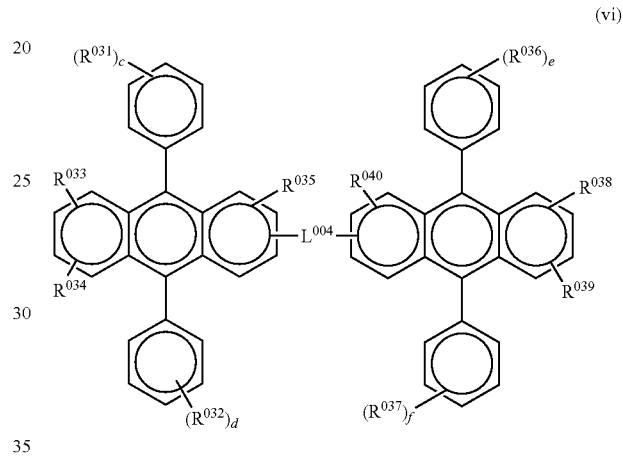

(vi)

wherein $R^{031}$ to $R^{040}$ are independently a hydrogen atom, an alkyl group, a cycloalkyl group, an aryl group, an alkoxy group, an aryloxy group, an alkylamino group, an arylamino group or a substituted or unsubstituted heterocyclic group, c, d, e and f are independently an integer of 1 to 5, and when they are two or more, $R^{031}$s, $R^{032}$s, $R^{036}$s or $R^{037}$s may be the same or different, $R^{031}$s, $R^{032}$s, $R^{033}$s or $R^{037}$s may be bonded to form a ring, and $R^{033}$ and $R^{034}$, and $R^{039}$ and $R^{040}$ may be bonded to each other to form a ring, and $L^{004}$ is a single bond, —O—, —S—, —N(R)— (R is an alkyl group or a substituted or unsubstituted aryl group), an alkylene group or an arylene group.

Spirofluorene derivative represented by the following formula (vii):

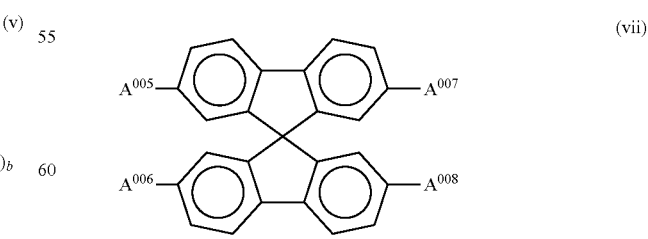

(vii)

wherein $A^{005}$ to $A^{008}$ are independently a substituted or unsubstituted biphenyl or a substituted or unsubstituted naphthyl group.

Fused ring-containing compounds shown by the following formula (viii):

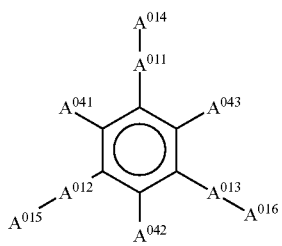

(viii)

wherein $A^{011}$ to $A^{013}$ represent the same divalent group as Li in the formula (1),
$A^{014}$ to $A^{016}$ represent the same substituent as $R_a$ in the formula (1), and
$R^{041}$ to $R^{043}$ are independently a hydrogen atom, alkyl group having 1 to 6 carbon atoms, cycloalkyl group having 3 to 6 carbon atoms, alkoxyl group having 1 to 6 carbon atoms, aryloxy group having 5 to 18 carbon atoms, aralkyloxy group having 7 to 18 carbon atoms, arylamino group having 5 to 16 carbon atoms, nitro group, cyano group, ester group having 1 to 6 carbon atoms, or a halogen atom, provided that at least one of $A^{011}$ to $A^{016}$ is a group having a fused aromatic ring with three or more rings.

Fluorene compounds shown by the following formula (ix):

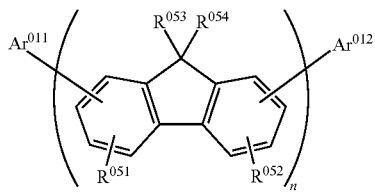

(ix)

wherein $R^{051}$ and $R^{052}$ are a hydrogen atom, a substituted or unsubstituted alkyl group, a substituted or unsubstituted aralkyl group, a substituted or unsubstituted aryl group, a substituted or unsubstituted heterocyclic group, substituted amino group, cyano group, or a halogen atom,
$R^{051}$s or $R^{052}$s bonded to different fluorene groups may be the same or different, and $R^{051}$ and $R^{052}$ bonded to a single fluorene group may be the same or different,
$R^{053}$ and $R^{054}$ are independently a hydrogen atom, a substituted or unsubstituted alkyl group, a substituted or unsubstituted aralkyl group, a substituted or unsubstituted aryl group or a substituted or unsubstituted heterocyclic group, $R^{053}$s or $R^{054}$s bonded to different fluorene groups may be the same or different, and $R^{053}$ and $R^{054}$ bonded to a single fluorene group may be the same or different,
$Ar^{011}$ and $Ar^{012}$ are a substituted or unsubstituted fused polycyclic aromatic group with a total number of benzene rings of three or more or a fused polycyclic heterocyclic group which is bonded to the fluorene group through substituted or unsubstituted carbon and has a total number of benzene rings and heterocyclic rings of three or more, provided that $Ar^{011}$ and $Ar^{012}$ may be the same or different, and
n is an integer of 1 to 10.

In the case of using a phosphorescent dopant, specific examples of the host compounds include carbazole, triazole, oxazole, oxadiazole, imidazole, polyarylalkane, pyrazoline, pyrazolone, phenylenediamine, arylamine, amino-substituted calcone, styrylanthracene, fluorenone, hydrazone, stilbene and silazane derivatives; aromatic tertiary amine, styrylamine, aromatic dimethylidene and porphyrin compounds, anthraquinodimethane, anthrone, diphenylquinone, thiopyrandioxide, carbodiimide, fluorenylidenemethane and distyrylpyrazine derivatives; heterocyclic tetracarboxylic anhydrides such as naphthaleneperylene, phthalocyanine derivatives, metal complexes of 8-quinolinol derivatives, various metal complex polysilane compounds represented by metal complexes having metalphthalocyanine, benzoxazole or benzothiazole as a ligand, electroconductive high molecular oligomers such as poly(N-vinylcarbazole) derivatives, aniline copolymers, thiophene oligomers and polythiophene, and polymer compounds such as polythiophene, polyphenylene, polyphenylenevinylene and polyfluorene derivatives. The host compounds may be used singly or in combination of two or more.

Specific examples include the following compounds.

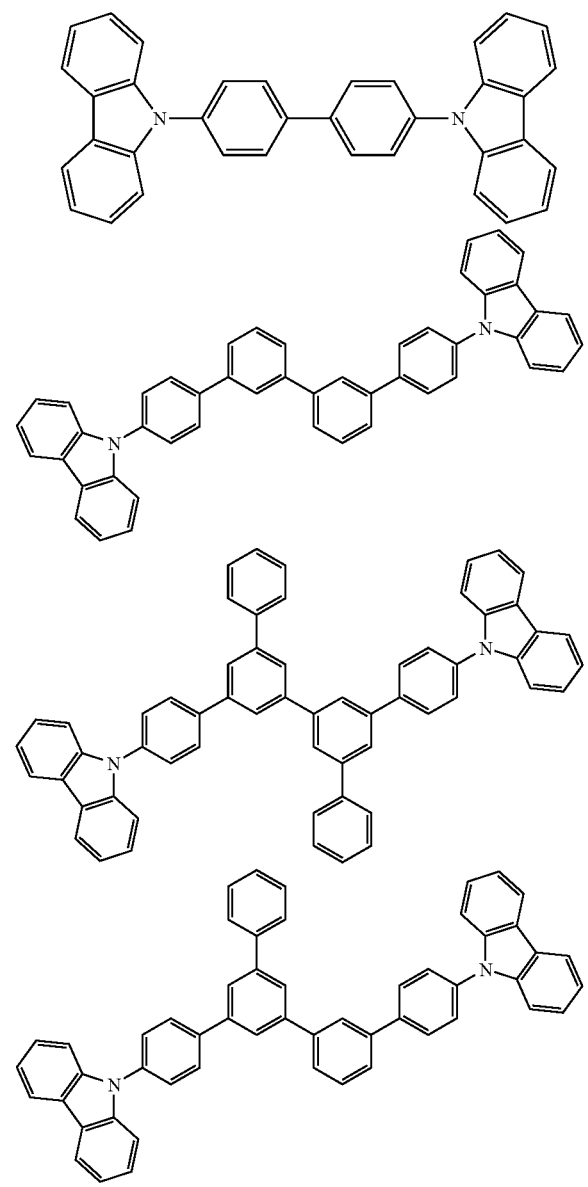

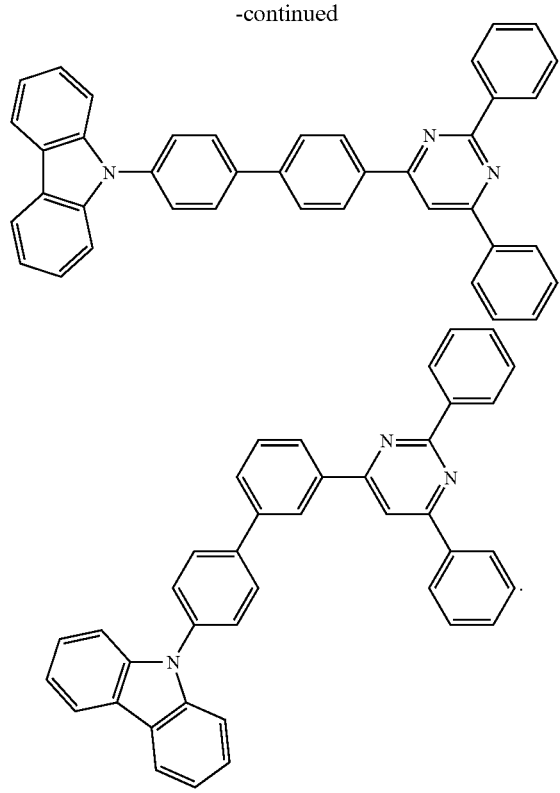

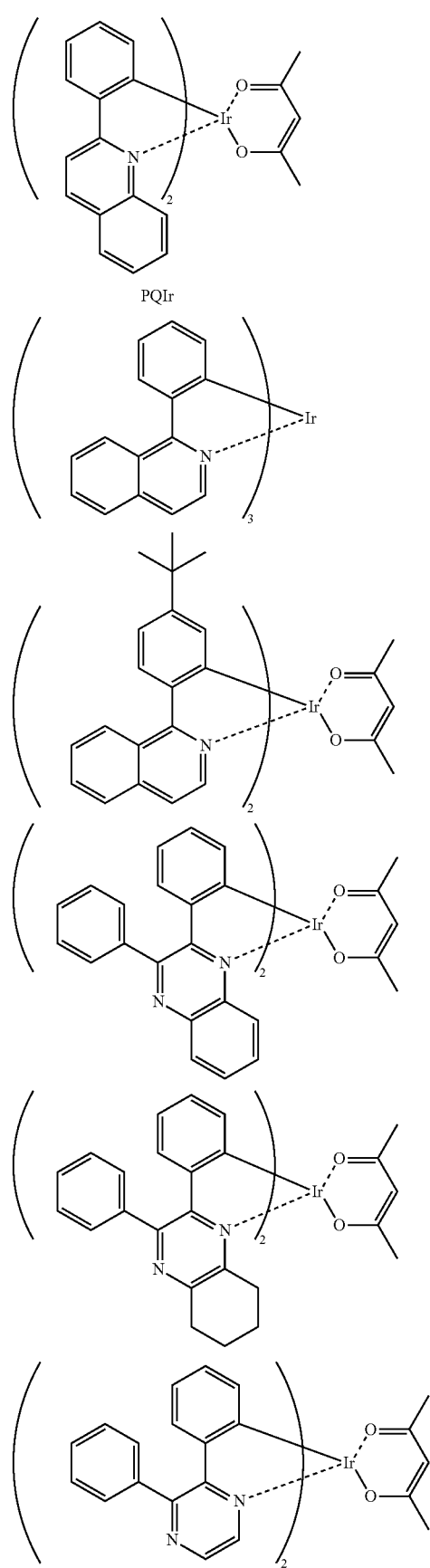

In the organic EL device of the invention, it is preferred that the emitting layer contain the emitting material of the invention as a host and contain at least one of a phosphorescent dopant and a fluorescent dopant. An emitting layer containing these dopants may be stacked on an emitting layer containing the compound of the invention.

A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable. The phosphorescent compounds can be used individually or as a combination of two or more kinds.

As a porphyrin metal complex, a porphyrin platinum complex is preferable.

There are various ligands forming an ortho-metalated metal complex. Preferable ligands include compounds having a phenylpyridine skeleton, a bipyridyl skeleton or a phenanthroline skeleton, 2-phenylpyridine, 7,8-benzoquinoline, 2-(2-thienyl)pyridine, 2-(1-naphthyl)pyridine and 2-phenylquinoline derivatives. These ligands may have a substituent, if necessary. Ligands to which fluorides, e.g. a trifluoromethyl group, being introduced as a substituent are particularly preferable as a blue dopant. As an auxiliary ligand, preferred are ligands other than the above-mentioned ligands, such as acetylacetonate and picric acid may be contained.

Specific examples of the metal complex include the following compounds. In the invention, it is preferred that the metal complex be combined with a phosphorescent dopant which gives emission in a red region. However, the metal complex is not limited thereto, and can be appropriately selected by the required emission color, the device performance and the host compound used.

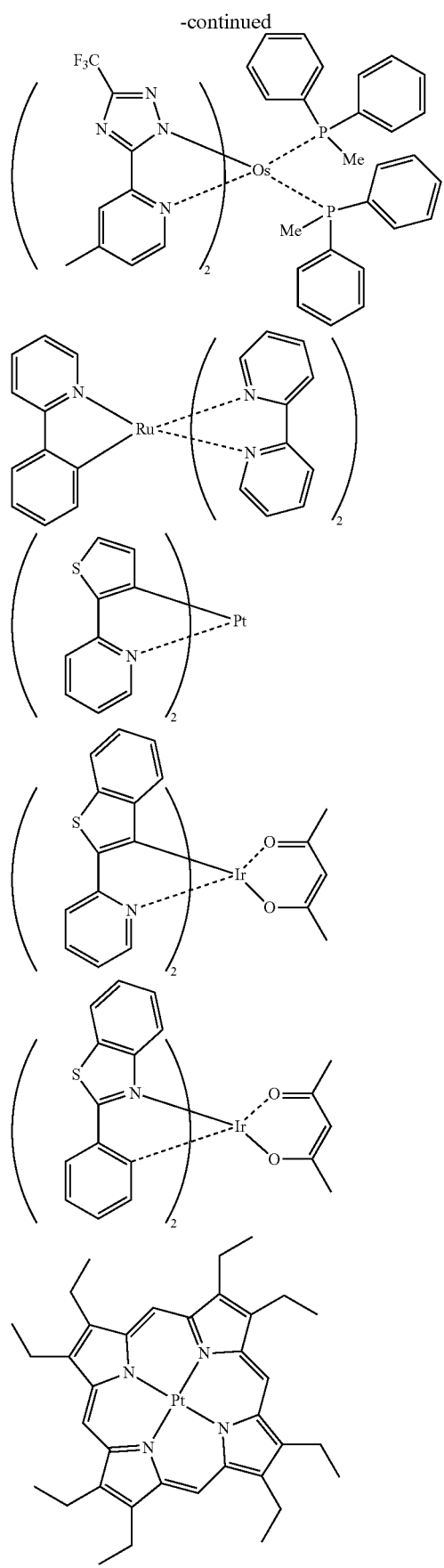
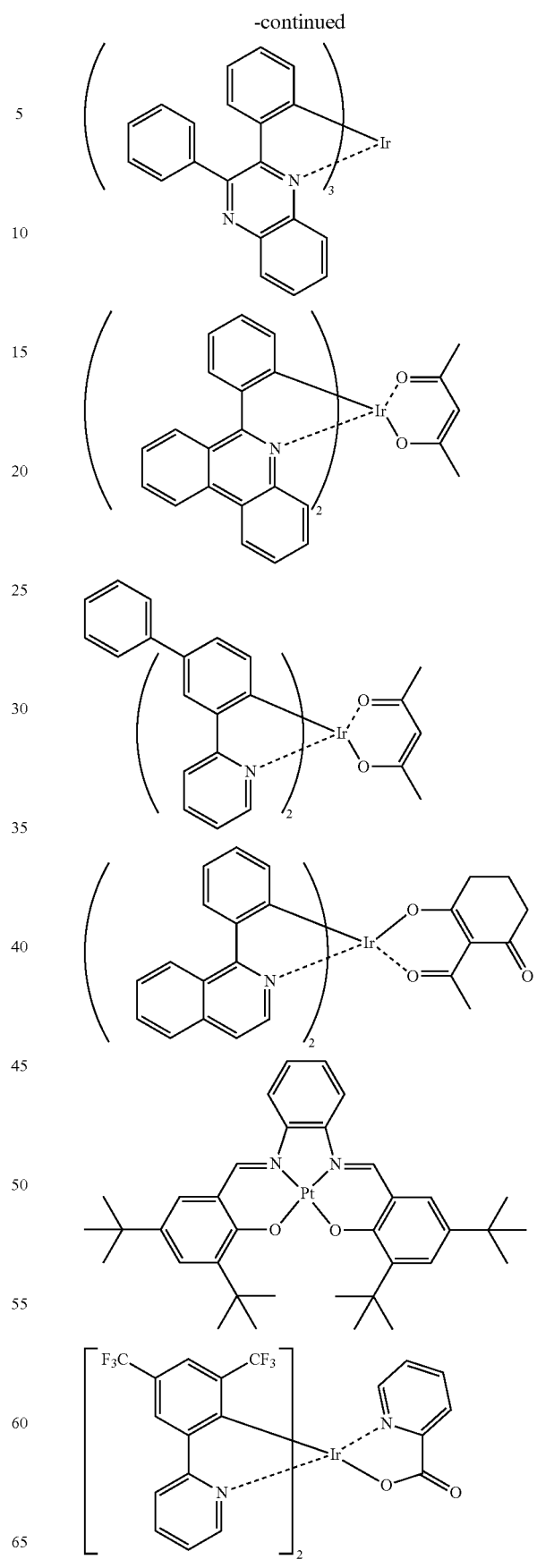

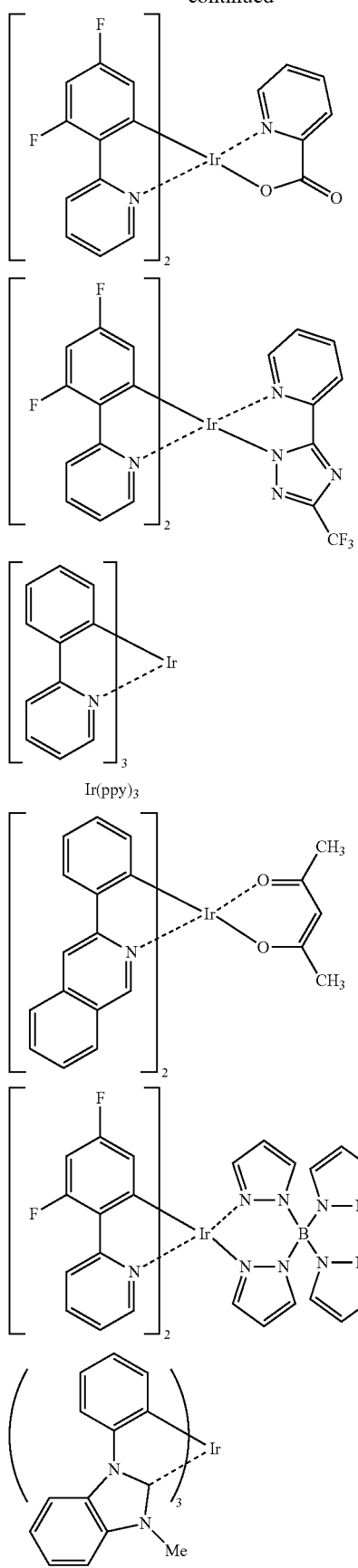

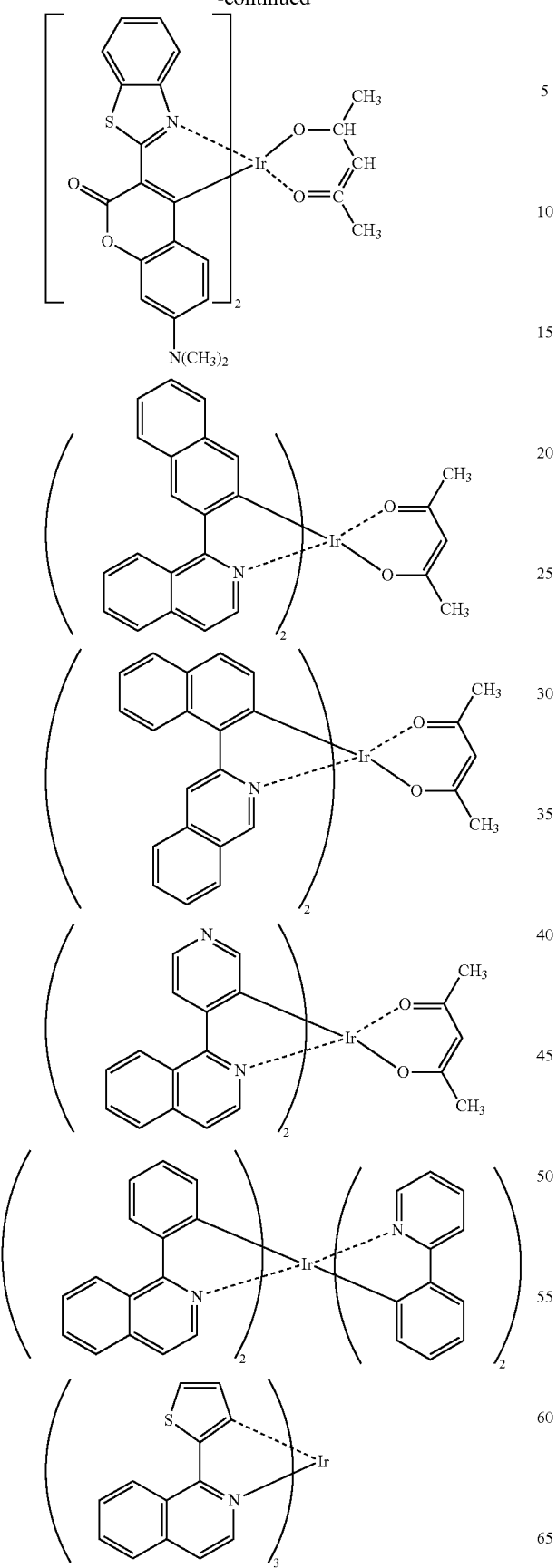
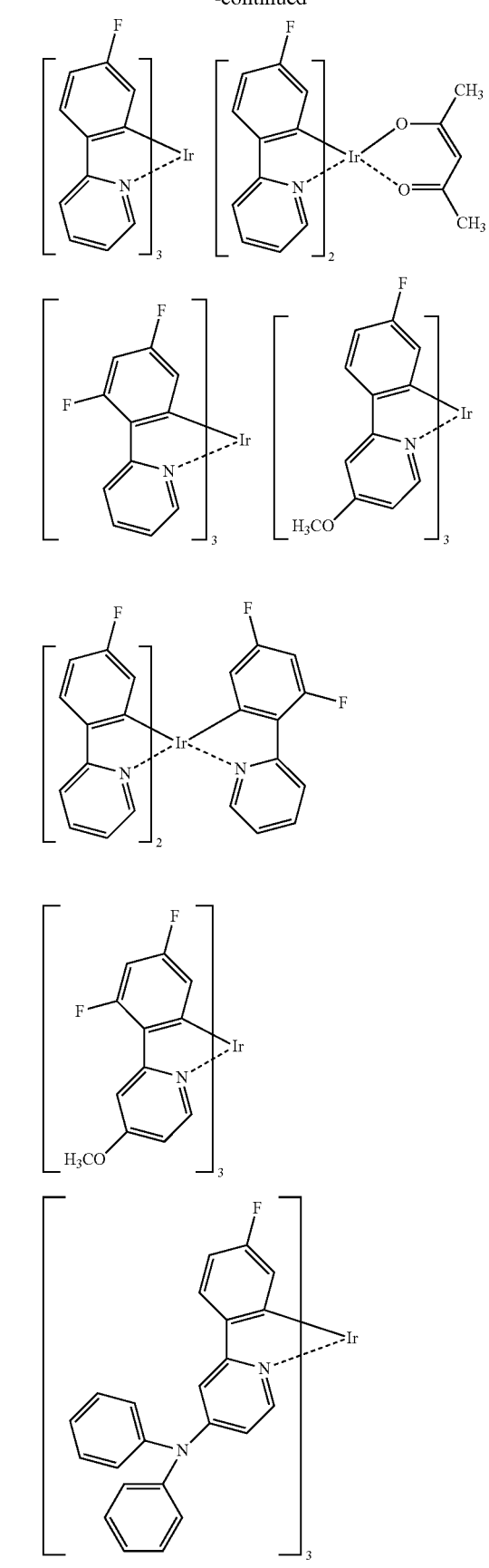

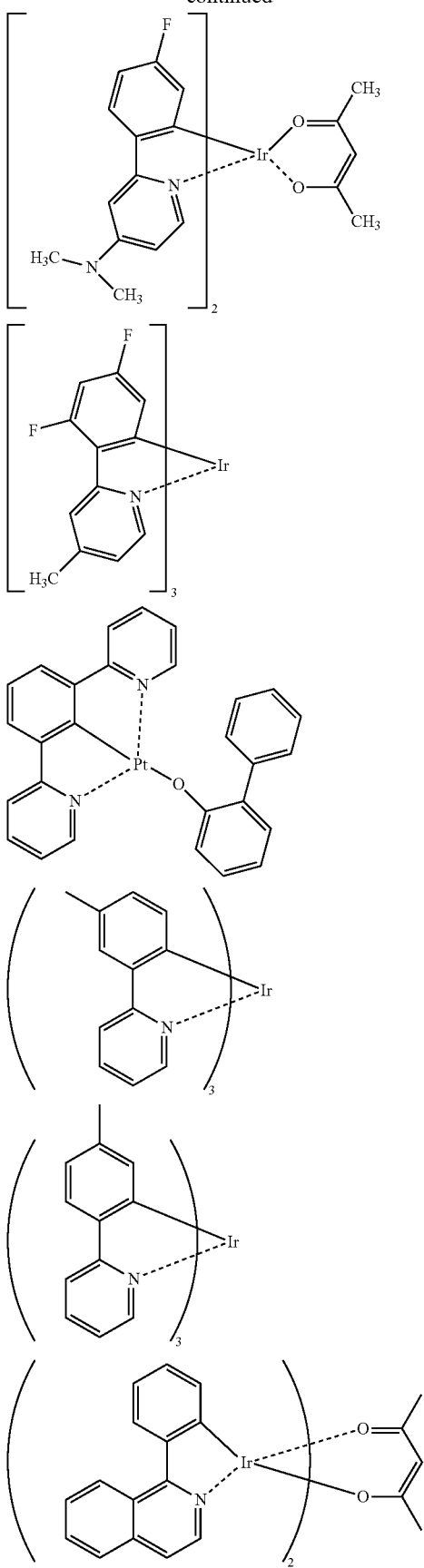
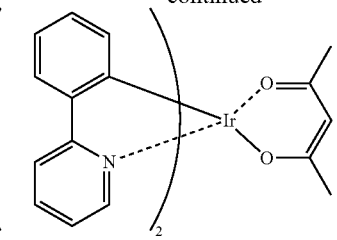

The content of a phosphorescent dopant in an emitting layer is not limited and can be properly selected according to purposes; for example, it is 0.1 to 70 mass %, preferably 1 to 30 mass %. When the content of a phosphorescent compound is less than 0.1 mass %, emission may be weak and the advantages thereof may not be sufficiently obtained. When the content exceeds 70 mass %, the phenomenon called concentration quenching may significantly proceed, thereby degrading the device performance.

As for the fluorescent dopant, it is preferable to select a compound from amine-based compounds, aromatic compounds, chelate complexes such as tris(8-quinolilate)aluminum complexes, coumarin derivatives, tetraphenylbutadiene derivatives, bisstyrylarylene derivatives, oxadiazole derivatives or the like, taking into consideration required emission colors. Of these, styrylamine compounds, styryldiamine compounds, arylamine compounds and aryldiamine compounds are further preferable. Fused polycyclic aromatic compounds which are not an amine compound are also preferable. These fluorescent dopants may be used singly or in combination of two or more.

The content of a fluorescent dopant in the emitting layer is not particularly limited and can be appropriately selected according to purposes; for example, it is 0.1 to 70 mass %, preferably 1 to 30 mass %.

As the styrylamine compound and the styryldiamine compound, those shown by the following formula (A) are preferable.

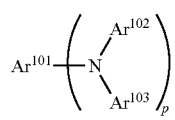

(A)

wherein $Ar^{101}$ is a group with a valence of p corresponding to a phenyl group, a naphthyl group, a biphenyl group, a terphenyl group, a stilbenzyl group or a distyrylaryl group, $Ar^{102}$ and $Ar^{103}$ are independently an aromatic hydrocarbon group having 6 to 20 carbon atoms, $Ar^{101}$, $Ar^{102}$ and $Ar^{103}$ may be substituted, one of $Ar^{101}$ to $Ar^{103}$ is substituted by a styryl group, further preferably, at least one of $Ar^{102}$ and $Ar^{103}$ is substituted by a styryl group, and p is an integer of 1 to 4, preferably an integer of 1 to 2.

Here, as the aromatic hydrocarbon group having 6 to 20 carbon atoms, a phenyl group, a naphthyl group, an anthranyl group, a phenanthryl group, a terphenyl group or the like can be given.

As the arylamine compound and the aryldiamine compound, those shown by the following formula (B) are preferable.

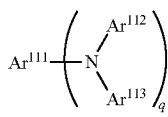
(B)

wherein $A^{111}$ is a substituted or unsubstituted aromatic group with a valence of q having 5 to 40 ring carbon atoms, $Ar^{112}$ and $Ar^{113}$ are independently a substituted or unsubstituted aryl group having 5 to 40 ring carbon atoms, and q is an integer of 1 to 4, preferably an integer of 1 to 2.

Examples of the aryl group having 5 to 40 ring carbon atoms include a phenyl group, a naphthyl group, an anthranyl group, a phenanthryl group, a pyrenyl group, a coronenyl group, a biphenyl group, a terphenyl group, a pyrrolyl group, a furanyl group, a thiophenyl group, a benzothiophenyl group, an oxadiazolyl group, a diphenylanthranyl group, an indolyl group, a carbazolyl group, a pyridyl group, a benzoquinolyl group, a fluoranthenyl group, an acenaphthofluoranthenyl group, a stilbene group, a perylenyl group, a chrysenyl group, a picenyl group, a triphenylenyl group, a rubicenyl group, a benzanthracenyl group, a phenylanthranyl group and a bisanthracenyl group. Preferred are a naphthyl group, an anthranyl group, chrysenyl group and a pyrenyl group.

As the $Ar^{111}$, the above-mentioned q-value group is preferable. When $Ar^{111}$ is a divalent group, groups shown by the following formulas (C) and (D) are preferable. A group shown by the formula (D) is more preferable.

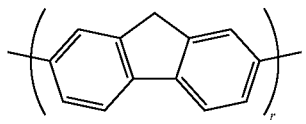
(C)

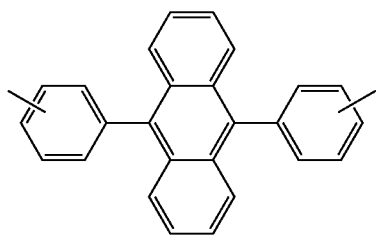
(D)

(in the formula (C), r is an integer of 1 to 3)

Preferred substituents for the above-mentioned aryl group include an alkyl group having 1 to 6 carbon atoms (ethyl, methyl, i-propyl, n-propyl, s-butyl, t-butyl, pentyl, hexyl, cyclopentyl, cyclohexyl, or the like); an alkoxy group having 1 to 6 carbon atoms (ethoxy, methoxy, i-propoxy, n-propoxy, s-buthoxy, t-buthoxy, penthoxy, hexyloxy, cyclopentoxy, cyclohexyloxy, or the like); an aryl group having 5 to 40 ring carbon atoms; an amino group substituted with an aryl group having 5 to 40 ring carbon atoms; an ester group with an aryl group having 5 to 40 ring carbon atoms; an ester group with an alkyl group having 1 to 6 carbon atoms; a cyano group; a nitro group; and a halogen atom.

The emitting layer may contain hole-transporting materials, electron-transporting materials and polymer binders, if necessary.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

The hole-transporting layer and the hole-injecting layer are layers which help the injection of holes into the emitting layer so as to transport holes to an emitting region, and have a large hole mobility and normally have such a small ionization energy as 5.5 eV or less. As the material for the hole-injecting layer and the hole-transporting layer, a material which transports holes to the emitting layer at a lower electrical field is preferable, and the hole mobility thereof is preferably $10^{-4}$ cm$^2$/V·second or more when an electric field of, e.g., $10^4$ to $10^6$ V/cm is applied.

There are no particular restrictions on the material for the hole-injecting layer and the hole-transporting layer. The material can be arbitrarily selected from materials which have been widely used as a hole-transporting material of photoconductive materials and known materials used in a hole-injecting layer and a hole-transporting layer of organic EL devices.

In the hole-injecting layer and the hole-transporting layer, an aromatic amine derivative shown by the following formula can be used, for example.

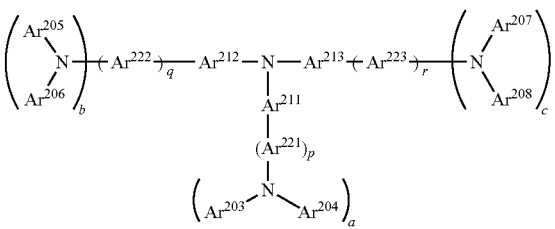

wherein $Ar^{211}$ to $Ar^{213}$, $Ar^{221}$ to $Ar^{223}$ and $Ar^{203}$ to $Ar^{208}$ are independently a substituted or unsubstituted aromatic hydrocarbon group having 6 to 50 ring carbon atoms or a substituted or unsubstituted aromatic heterocyclic group having 5 to 50 ring atoms, a to c and p to r are independently an integer of 0 to 3, and $Ar^{203}$ and $Ar^{204}$, $Ar^{205}$ and $Ar^{206}$, or $Ar^{207}$ and $Ar^{208}$ may be bonded to each other to form a saturated or unsaturated ring.

Examples of the substituted or unsubstituted aromatic ring groups having 6 to 50 ring carbon atoms include a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, and 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

Examples of the substituted or unsubstituted aromatic heterocyclic group having 5 to 50 ring atoms include a 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 10-phenothiadinyl group, 1-phenoxadinyl group, 2-phenoxadinyl group, 3-phenoxadinyl group, 4-phenoxadinyl group, 10-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Further, the compound shown by the following formula can be used in the hole-injecting layer and the hole-transporting layer.

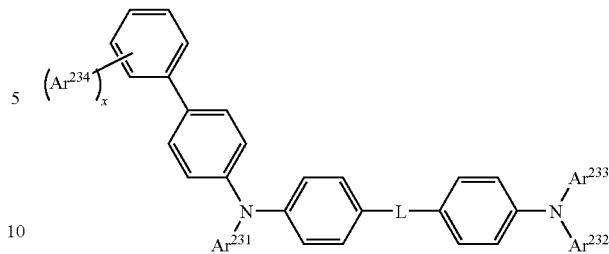

wherein $Ar^{231}$ to $Ar^{234}$ are independently a substituted or unsubstituted aromatic hydrocarbon group having 6 to 50 ring carbon atoms, or a substituted or unsubstituted aromatic heterocyclic group having 5 to 50 ring atoms, L is a linking group, which is a single bond, a substituted or unsubstituted aromatic hydrocarbon group having 6 to 50 ring carbon atoms or a substituted or unsubstituted aromatic heterocyclic group having 5 to 50 ring atoms, x is an integer of 0 to 5, and $Ar^{232}$ and $Ar^{233}$ may be bonded to each other to form a saturated or unsaturated ring.

As specific examples of the substituted or unsubstituted aromatic hydrocarbon group having 6 to 50 ring carbon atoms and substituted or unsubstituted aromatic heterocyclic group having 5 to 50 ring atoms, the same as those exemplified above for the aromatic amine derivative can be given.

As specific examples of the material for the hole-injecting layer and the hole-transporting layer, a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalkone derivative, an oxazole derivative, a styrylanthracene derivative, a fluorenone derivative, a hydrazone derivative, a stilbene derivative, a silazane derivative, an aniline-based copolymer, and conductive high-molecular oligomers (in particular, a thiophene oligomer) can be given.

As the material for the hole-injecting layer and the hole-transporting layer, although the above-mentioned materials can be used, it is preferable to use a porphyrin compound, an aromatic tertiary amine compound and a styrylamine compound. It is particularly preferable to use an aromatic tertiary amine compound.

It is preferable to use a compound having two fused aromatic rings in the molecule thereof, for example, 4,4'-bis(N-(1-naphthyl)-N-phenylamino)biphenyl (abbreviated by NPD, hereinafter), and 4,4',4"-tris(N-(3-methylphenyl)-N-phenylamino)triphenylamine (abbreviated by MTDATA, hereinafter) wherein three triphenylamine units are linked in a star-burst form.

In addition to the above, a nitrogen-containing heterocyclic derivative shown by the following formula can also be used.

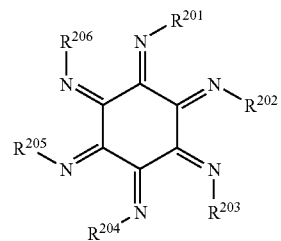

wherein $R^{201}$ to $R^{206}$ are independently a substituted or unsubstituted alkyl group, a substituted or unsubstituted aryl group, a substituted or unsubstituted aralkyl group, a substituted or unsubstituted heterocyclic group, and $R^{201}$ and $R^{202}$, $R^{203}$ and $R^{204}$, $R^{205}$ and $R^{206}$, $R^{201}$ and $R^{206}$, $R^{202}$ and $R^{203}$, or $R^{204}$ and $R^{205}$ may form a fused ring.

Further, the following compound can also be used.

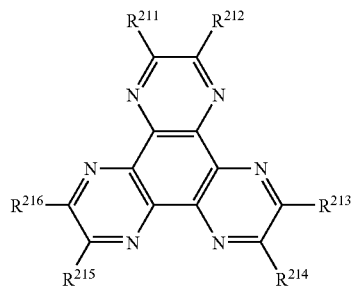

wherein $R^{211}$ to $R^{216}$ are substituents; preferably they are independently an electron-attracting group such as a cyano group, a nitro group, a sulfonyl group, a carbonyl group, a trifluoromethyl group and a halogen.

Further, an inorganic compound such as p-type Si and p-type SiC can also be used as a material for the hole-injecting layer and the hole-transporting layer.

The hole-injecting layer and the hole-transporting layer can be formed from the above-mentioned compounds by a known method such as vapor vacuum deposition, spin coating, casting or LB technique. The film thickness of the hole-injecting layer and the hole-transporting layer is not particularly limited, and is usually from 5 nm to 5 μm. The hole-injecting layer and the hole-transporting layer may be a single layer made of one or two or more of the above-mentioned materials, or may be of a structure in which hole-injecting layers and hole-transporting layers made of different compounds are stacked.

The organic semiconductor layer is a layer for helping the injection of holes or electrons into the emitting layer, and is preferably a layer having an electric conductivity of $10^{-10}$ S/cm or more. As the material of such an organic semiconductor layer, electroconductive oligomers such as thiophene-containing oligomers or arylamine-containing oligomers and electroconductive dendrimers such as arylamine-containing dendrimers may be used.

The electron-injecting layer and the electron-transporting layer are layers which assist injection of electrons into the emitting layer and transport electrons to the emitting region, and exhibit a high electron mobility. The adhesion-improving layer is a kind of the electron-injecting layer which is made of a material exhibiting particularly good adhesion to the cathode.

The thickness of the electron-transporting layer is arbitrarily selected in the range of 5 nm to 5 μm. When the electron-transporting layer has a thick thickness, it is preferable that the electron mobility be $10^{-5}$ cm$^2$/Vs or more at an applied electric field of $10^4$ to $10^6$ V/cm in order to prevent an increase in voltage.

The material used in the electron-injecting layer and the electron-transporting layer is preferably a metal complex of 8-hydroxyquinoline or a derivative thereof, or an oxadiazole derivative. Specific examples of the metal complex of 8-hydroxyquinoline or derivative thereof include metal chelate oxynoid compounds containing a chelate of oxine (generally, 8-quinolinol or 8-hydroxyquinoline), e.g. tris(8-quinolinolato)aluminum.

As examples of the oxadiazole derivative, an electron-transporting compound shown by the following formula can be given.

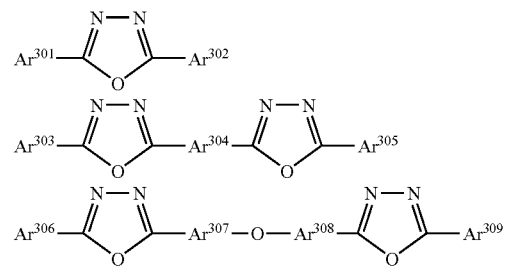

wherein $Ar^{301}$, $Ar^{302}$, $Ar^{303}$, $Ar^{305}$, $Ar^{306}$ and $Ar^{309}$ are independently a substituted or unsubstituted aryl group, and $Ar^{304}$, $Ar^{307}$ and $Ar^{308}$ are independently a substituted or unsubstituted arylene group.

As examples of the aryl group, a phenyl group, a biphenyl group, an anthranyl group, a perylenyl group, and a pyrenyl group can be given. As examples of the arylene group, a phenylene group, a naphthylene group, a biphenylene group, an anthranylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron-transporting compound is preferably one from which a thin film can be formed.

The following compounds can be given as specific examples of the electron-transporting compound.

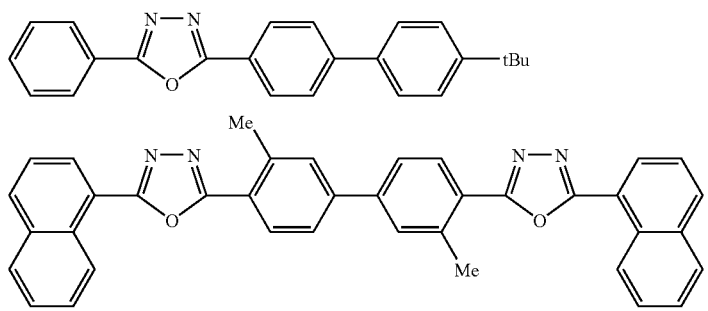

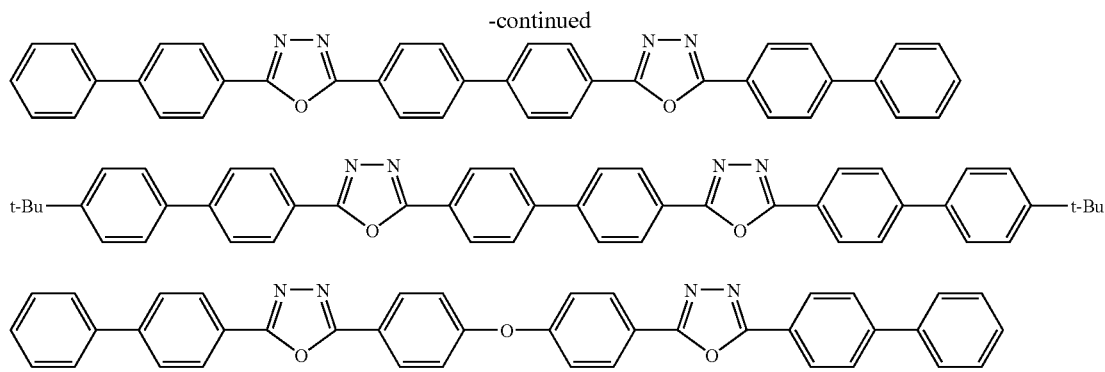

(Me is methyl and tbu is t-butyl.)

Furthermore, as materials used for the electron-injecting layer and electron-transporting layer, the compounds represented by the following formulas (E) to (J) may be used.

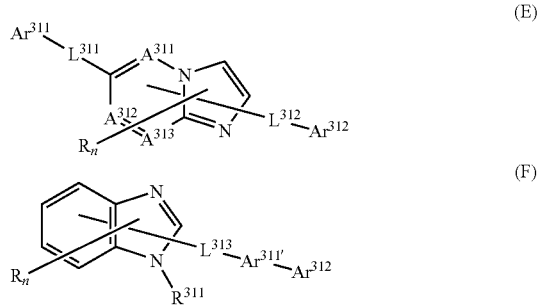

Nitrogen-containing heterocyclic derivatives shown by the formulas (E) and (F):

wherein $Ar^{311}$ to $Ar^{313}$ are independently a nitrogen atom or a carbon atom, $Ar^{311}$ is a substituted or unsubstituted aryl group having 6 to 60 ring carbon atoms or a substituted or unsubstituted heteroaryl group having 3 to 60 ring atoms, $Ar^{311'}$ is an arylene group having 6 to 60 ring carbon atoms or a substituted or unsubstituted heteroarylene group having 3 to 60 ring atoms, and $Ar^{312}$ is a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 carbon atoms, or a substituted or unsubstituted alkoxy group having 1 to 20 carbon atoms, provided that one of $Ar^{311}$ and $Ar^{312}$ is a substituted or unsubstituted fused ring group having 10 to 60 ring carbon atoms or a substituted or unsubstituted monohetero fused ring group having 3 to 60 ring atoms, $L^{311}$, $L^{312}$ and $L^{313}$ are independently a single bond, a substituted or unsubstituted arylene group having 6 to 60 ring carbon atoms, a substituted or unsubstituted heteroarylene group having 3 to 60 ring atoms, or a substituted or unsubstituted fluorenylene group, R and $R^{311}$ are independently a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 carbon atoms, or a substituted or unsubstituted alkoxy group having 1 to 20 carbon atoms, n is an integer of 0 to 5, and when n is two or more, plural Rs may be the same or different, and adjacent Rs may be bonded to each other to form a carbocyclic aliphatic ring or a carbocyclic aromatic ring.

$$HAr\text{-}L^{314}\text{-}Ar^{321}\text{-}Ar^{322} \qquad (G)$$

Nitrogen-containing heterocyclic derivatives shown by formula (G):

wherein HAr is a nitrogen-containing heterocyclic ring having 3 to 40 carbon atoms, which may have a substituent, $L^{314}$ is a single bond, an arylene group having 6 to 60 carbon atoms, which may have a substituent, an heteroarylene group having 3 to 60 atoms, which may have a substituent, or a fluorenylene group which may have a substituent, $Ar^{321}$ is a divalent aromatic hydrocarbon group having 6 to 60 carbon atoms, which may have a substituent, and $Ar^{322}$ is a an aryl group having 6 to 60 carbon atoms, which may have a substituent or a heteroaryl group having 3 to 60 atoms, which may have a substituent.

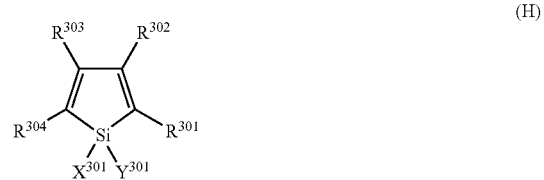

Silacyclopentadiene derivatives shown by the formula (H) wherein $X^{301}$ and $Y^{301}$ are independently a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted hetero ring, or X and Y are bonded to form a saturated or unsaturated ring, and $R^{301}$ to $R^{304}$ are independently hydrogen, halogen, an alkyl group, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group. These groups may be substituted and adjacent groups may form a substituted or unsubstituted fused ring.

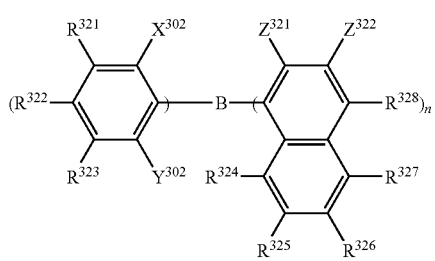 (I)

Borane derivatives shown by the formula (I) wherein $R^{321}$ to $R^{328}$ and $Z^{322}$ are independently a hydrogen atom, a saturated or unsaturated hydrocarbon group, an aromatic hydrocarbon group, a heterocyclic group, a substituted amino group, a substituted boryl group, an alkoxy group, or an aryloxy group, $X^{302}$, $Y^{302}$, and $Z^{321}$ are independently a saturated or unsaturated hydrocarbon group, an aromatic hydrocarbon group, a heterocyclic group, a substituted amino group, an alkoxy group, or an aryloxy group, $Z^{321}$ and $Z^{322}$ may be bonded to form a fused ring, and n is an integer of 1 to 3, provided that when n or (3-n) is two or more, $R^{321}$ to $R^{328}$, $X^{302}$, $Y^{302}$, $Z^{322}$ and $Z^{321}$ may be the same or different, provided that compounds where n is 1, $X^{302}$, $Y^{302}$, and $R^{322}$ are methyl groups, and $R^{328}$ is a hydrogen atom or a substituted boryl group, and compounds where n is 3 and $Z^{321}$ is a methyl group are excluded.

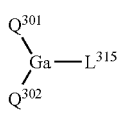 (J)

Gallium complexes shown by the formula (J) wherein $Q^{301}$ and $Q^{302}$ are independently ligands represented by the following formula (K) and $L^{315}$ is a halogen atom, a substituted or unsubstituted alkyl group, a substituted or unsubstituted cycloalkyl group, a substituted or unsubstituted aryl group, a substituted or unsubstituted heterocyclic group, —OR(R is a hydrogen atom, a substituted or unsubstituted alkyl group, a substituted or unsubstituted cycloalkyl group, a substituted or unsubstituted aryl group, or a substituted or unsubstituted heterocyclic group) or a ligand represented by —O—Ga—$Q^{303}(Q^{304})$ wherein $Q^{303}$ and $Q^{304}$ are the same as $Q^{301}$ and $Q^{302}$.

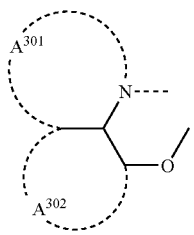 (K)

wherein rings $A^{301}$ and $A^{302}$ are independently a 6-membered aryl ring structure which may have a substituent and they are fused to each other.

The metal complexes have the strong nature of an n-type semiconductor and large ability of injecting electrons. Further, the energy generated at the time of forming a complex is small so that a metal is then strongly bonded to ligands in the complex formed and the fluorescent quantum efficiency becomes large as the emitting material.

Specific examples of the substituents for the rings $A^{301}$ and $A^{302}$ forming the ligand of the formula (K) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, substituted or unsubstituted aryl groups such as a phenyl group, naphthyl group, biphenyl group, anthranyl group, phenanthryl group, fluorenyl group, pyrenyl group, 3-methylphenyl group, 3-methoxyphenyl group, 3-fluorophenyl group, 3-trichloromethylphenyl group, 3-trifluoromethylphenyl group, and 3-nitrophenyl group, substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, substituted or unsubstituted aryloxy groups such as a phenoxy group, p-nitrophenoxy group, p-tert-butylphenoxy group, 3-fluorophenoxy group, pentafluorophenyl group, and 3-trifluoromethylphenoxy group, substituted or unsubstituted alkylthio groups such as a methylthio group, ethylthio group, tert-butylthio group, hexylthio group, octylthio group, and trifluoromethylthio group, substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, diethylamino group, ethylamino group, diethylamino group, dipropylamino group, dibutylamino group, and diphenylamino group, acylamino groups such as a bis(acetoxymethyl)amino group, bis(acetoxyethyl)amino group, bis(acetoxypropyl) amino group, and bis(acetoxybutyl)amino group, a hydroxyl group, a siloxy group, an acyl group, substituted or unsubstituted carbamoyl groups such as a carbamoyl group, methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imide group, cycloalkyl groups such as a cyclopentane group and cyclohexyl group, heterocyclic groups such as a pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, carbazolyl group, furanyl group, thiophenyl group, oxazolyl group, oxadiazolyl group, benzoxazolyl group, thiazolyl group, thiadiazolyl group, benzothiazolyl group, triazolyl group, imidazolyl group, and benzimidazolyl group. The above substituents may be bonded to form a further six-membered aryl ring or heterocyclic ring.

A preferred embodiment of the organic EL device is a device containing a reducing dopant in an electron-transferring region or in an interfacial region between a cathode and an organic layer. The reducing dopant is defined as a substance which can reduce an electron-transferring compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal carbonates, alkaline earth metal carbonates, rare earth metal carbonates, alkali metal organic complexes, alkaline earth metal organic complexes, and rare earth metal organic complexes.

More specific examples of the preferred reducing dopants include at least one alkali metal selected from the group consisting of Na (work function: 2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV). Metals having a work function of 2.9 eV or less are particularly preferred. Among these, a more preferable reducing dopant is at least one alkali metal selected from the group consisting of K, Rb and Cs. Even more preferable is Rb or Cs. Most preferable is Cs. These alkali metals are particularly high in reducing ability. Thus, the addition of a relatively small amount thereof to an electron-injecting zone improves the luminance of the organic EL device and make the lifetime thereof long. As a reducing agent having a work function of 2.9 eV or less, combinations of two or more alkali metals are preferable, particularly combinations including Cs, such as Cs and Na, Cs and K, Cs and Rb, or Cs, Na and K are preferable. The combination containing Cs makes it possible to exhibit the reducing ability efficiently. The luminance of the organic EL device can be improved and the lifetime thereof can be made long by the addition thereof to its electron-injecting zone.

An electron-injecting layer made of an insulator or a semiconductor may further be provided between a cathode and an organic layer. By forming the electron-injecting layer, a current leakage can be effectively prevented and electron-injecting properties can be improved. If the electron-injecting layer is an insulating thin film, more uniformed thin film can be formed whereby pixel defects such as a dark spot are decreased.

As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved. Specifically preferable alkali metal calcogenides include $Li_2O$, $K_2O$, $Na_2S$, $Na_2Se$ and $Na_2O$ and preferable alkaline earth metal calcogenides include CaO, BaO, SrO, BeO, BaS and CaSe. Preferable halides of alkali metals include LiF, NaF, KF, CsF, LiCl, KCl and NaCl. Preferable halides of alkaline earth metals include fluorides such as $CaF_2$, $BaF_2$, $SrF_2$, $MgF_2$ and $BeF_2$ and the other halides corresponding to the fluorides.

Semiconductors forming an electron-injecting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn. An inorganic compound forming an electron-injecting layer is preferably a microcrystalline or amorphous insulating thin film.

For the cathode, the following may be used: an electrode substance made of a metal, an alloy or an electroconductive compound, or a mixture thereof which has a small work function (for example, 4 eV or less). Specific examples of the electrode substance include sodium, sodium-potassium alloy, magnesium, lithium, cesium, magnesium/silver alloy, aluminum/aluminum oxide, $Al/Li_2O$, Al/LiO, Al/LiF, aluminum/lithium alloy, indium, and rare earth metals.

The cathode is formed from these electrode materials by vapor deposition, sputtering or the like.

In the case where emission from the emitting layer is out-coupled through the cathode, it is preferred to make the transmittance of the cathode to the emission larger than 10%. The sheet resistance of the cathode is preferably several hundreds $\Omega/\square$ or less, and the film thickness thereof is usually from 10 nm to 1 μm, preferably from 50 to 200 nm.

Generally, in the organic EL device, pixel defects based on leakage or a short circuit are easily generated since an electric field is applied to the super thin film. In order to prevent this, it is preferred to insert an insulating thin layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or laminate thereof may be used.

As for the method for fabricating the organic EL device, it can be fabricated by forming necessary layers sequentially from the anode using the materials and the method as mentioned above, and finally forming the cathode. The organic EL device can be fabricated in the order reverse to the above, i.e., the order from the cathode to the anode.

An example of the fabrication of the organic EL device will be described below which has a structure wherein the following are successively formed on a transparent substrate: anode/hole-injecting layer/emitting layer/electron-injecting layer/cathode.

At first, a thin film formed of an anode material is formed on a transparent substrate by vapor deposition or sputtering to form an anode.

Next, a hole-injecting layer is formed on this anode. As described above, the hole-injecting layer can be formed by vacuum deposition, spin coating, casting, LB technique, or some other method. Vacuum deposition is preferred since a homogenous film is easily obtained and pinholes are not easily generated. In the case where the hole-injecting layer is formed by vacuum deposition, conditions for the deposition vary depending upon a compound used (a material for the hole-injecting layer), a desired structure of the hole-injecting layer, and others. In general, the conditions are preferably selected from the following: deposition source temperature of 50 to 450° C., vacuum degree of $10^{-7}$ to $10^{-3}$ Torr, vapor deposition rate of 0.01 to 50 nm/second, and substrate temperature of −50 to 300° C.

Next, an emitting layer is formed on the hole-injecting layer. The emitting layer can also be formed by making a luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vacuum vapor deposition, conditions for the deposition, which vary depending on a compound used, can be generally selected from conditions similar to those for the hole-injecting layer.

Next, an electron-injecting layer is formed on the emitting layer. Like the hole-injecting layer and the emitting layer, the layer is preferably formed by vacuum vapor deposition because a homogenous film is required. Conditions for the deposition can be selected from conditions similar to those for the hole-injecting layer and the emitting layer.

Lastly, a cathode is stacked thereon to obtain an organic EL device. The cathode can be formed by vapor deposition or sputtering. However, vapor vacuum deposition is preferred in order to protect underlying organic layers from being damaged when the cathode film is formed.

For the organic EL device fabrication described above, it is preferred that the formation from the anode to the cathode is continuously carried out, using only one vacuuming operation.

The method for forming each of the layers in the organic EL device is not particularly limited. An organic thin film layer containing the compound of the invention can be formed by a known method such as vacuum vapor deposition, molecular beam epitaxy (MBE), or an applying coating method using a solution in which the compound is dissolved in a solvent, such as dipping, spin coating, casting, bar coating, or roll coating.

EXAMPLES

The invention will be explained in more detail with reference to the following examples.

Synthesis Example 1

Benzo[g]chrysene was synthesized according to the following synthesis scheme.

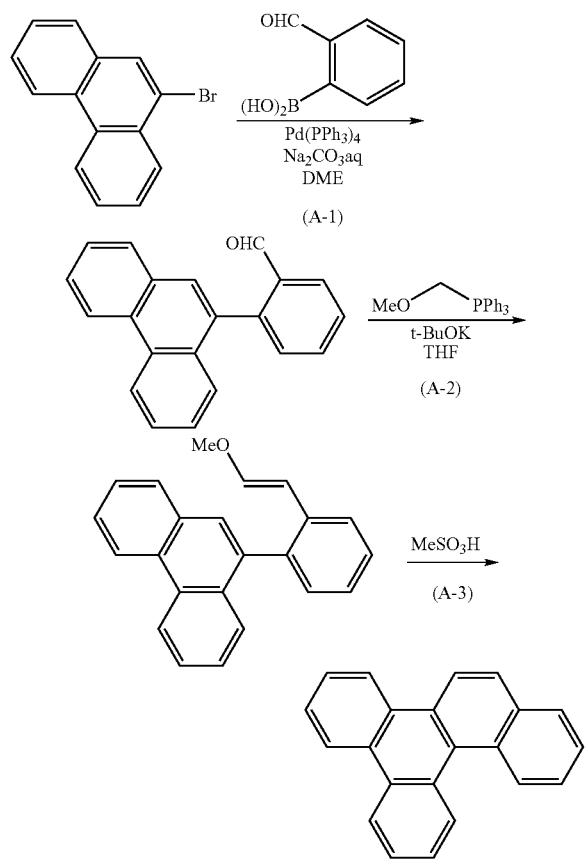

(A-1) Synthesis of 9-(2-formylphenyl)phenanthrene

Under an argon atmosphere, 25.7 g of 9-bromophenanthrene, 16.5 g of 2-formylphenylboronic acid and 2.31 g of tetraxis(triphenylphosphine)palladium(0) were placed in a flask. 340 mL of dimethoxyethane (DME) and 170 mL of a 2M aqueous sodium carbonate solution were added to this flask, and the resultant was refluxed with stirring while heating for 8 hours. After cooling to room temperature, an aqueous phase was removed. An organic phase was washed with water and saturated brine, and then dried with magnesium sulfate. After the magnesium sulfate was filtered out, the organic phase was concentrated. The residue was purified by means of silica gel column chromatography, whereby 25.0 g (yield: 89%) of intended 9-(2-formylphenyl)phenanthrene was obtained.

(A-2) Synthesis of 9-[1-(2-methoxyvinyl)phenyl]phenanthrene

Under an argon atmosphere, 25.0 g of 9-(2-formylphenyl)phenanthrene, 33.4 g of methoxymethyltriphenylphosphonium chloride and 300 mL of tetrahydrofuran (THF) were placed in a flask. During stirring at room temperature, 11.9 g of potassium t-butoxide was added to the flask. After further stirring at room temperature for 2 hours, 200 mL of water was added. The reaction solution was extracted with diethyl ether. An aqueous phase was removed and an organic phase was washed with water and saturated brine, and then dried with magnesium sulfate. After the magnesium sulfate was filtered out, the organic phase was concentrated. The resulting residue was purified by means of silica gel column chromatography, whereby 24.0 g (yield: 87%) of intended 9-[1-(2-methoxyvinyl)phenyl]phenanthrene was obtained.

(A-3) Synthesis of benzo[g]chrysene 24.0 g of 9-[1-(2-methoxyvinyl)phenyl]phenanthrene and 100 mL of dichloromethane were placed in a flask. During stirring at room temperature, 6 drops of methanesulfonic acid were added to the flask by means of a Pasteur pipette. Stirring was conducted at room temperature for further 8 hours. After the completion of the reaction, 100 mL of a 10% aqueous solution of potassium carbonate was added. An aqueous phase was removed and an organic phase was washed with water and saturated brine, and then dried with magnesium sulfate. After the magnesium sulfate was filtered out, the organic phase was concentrated. The residue was purified by means of silica gel column chromatography, whereby 5.21 g (yield: 25%) of intended benzo[g]chrysene was obtained.

Synthesis Example 2

Benzo[g]chrysene-10-boronic acid, which would be an intermediate of the compound of the invention, was synthesized from the benzo[g]chrysene.

(B-1) Synthesis of 10-bromobenzo[g]chrysene 5.21 g of the benzo[g]chrysene and 50 mL of N,N-dimethylformamide were placed in a flask. 10 mL of a N,N-dimethylformamide solution of 4.00 g of N-bromosuccinimido was added. The resultant was heated with stirring at 80° C. for 8 hours. After cooling to room temperature, the reaction solution was poured to 200 mL of water. Deposited solids were separated by filtration, and washed with water and with methanol. The thus obtained solids were purified by means of silica gel column chromatography, whereby 5.87 g (yield: 88%) of 10-bromobenzo[g]chrysene was obtained.

(B-2) Synthesis of benzo[g]chrysene-10-boronic acid

Under an atmosphere of argon, 5.87 g of 10-bromobenzo[g]chrysene was placed in a flask. Then, 200 mL of dehydrated ether and 200 mL of dehydrated toluene were added. After cooling the reaction solution to −40° C., 11 mL of a 1.6M hexane solution of n-butyl lithium was added, and the temperature was elevated to 0° C., followed by stirring for 1 hour. After cooling the reaction solution to −60° C., 10 mL of a dehydrated ether solution of 7.72 g of triisopropyl borate was added dropwisely. The stirring was conducted for 5 hours while heating the reaction solution to room temperature.

Then, 100 ml of an aqueous 10% hydrochloric solution was added, followed by stirring for 1 hour. An aqueous phase was removed and an organic phase was washed with water and saturated brine, and then dried with magnesium sulfate. After the magnesium sulfate was filtered out, the organic phase was concentrated. The resulting solids were washed with hexane, whereby 3.18 g (yield: 60%) of intended benzo[g]chrysene-10-boronic acid was obtained.

[Synthesis of a Fused Aromatic Ring Derivative]

Example 1

The following compound 1 was synthesized by the following reaction.

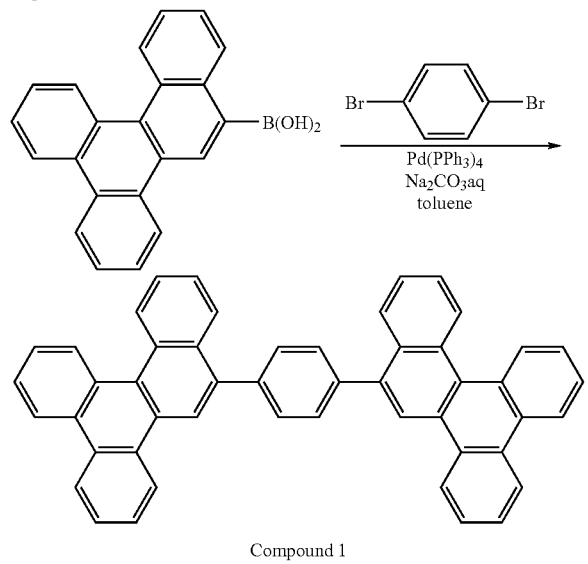

Compound 1

Under an argon atmosphere, 7.72 g of the benzo[g]chrysene-10-boronic acid, 2.36 g of 1,4-dibromobenzene, 0.462 g of tetraxis(triphenylphosphine)palladium(0), 80 mL of toluene and 40 mL of a 2M aqueous solution of sodium carbonate were placed in a flask. The resultant was refluxed with stirring for 8 hours. After cooling to room temperature, the reaction solution was extracted with toluene. An aqueous phase was removed, and an organic phase was washed with water and then with saturated brine, and dried with magnesium sulfate. After the magnesium sulfate was filtered out, the organic phase was concentrated. The residue was purified by a silica gel column chromatography, whereby 5.04 g of white crystals were obtained. As a result of mass spectrometry, the resulting crystals were confirmed to be an intended product. This intended product had an m/z value of 630 with respect to a molecular weight of 630.23.

Example 2

The following compound 2 was synthesized by the following reaction.

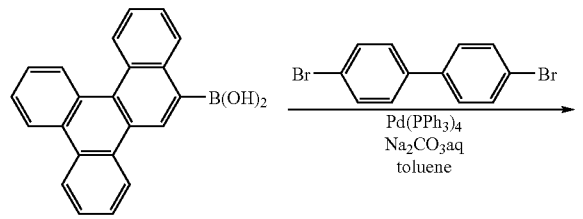

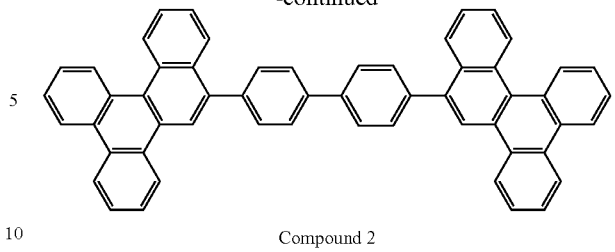

Compound 2

A compound was synthesized in the same manner as in Example 1, except that 4,4'-dibromobiphenyl was used instead of 1,4-dibromobenzene. As a result of mass spectroscopy, the resulting compound was confirmed to be an intended product. This intended product had an m/z value of 706 with respect to a molecular weight of 706.27.

Example 3

The following compound 3 was synthesized by the following reaction.

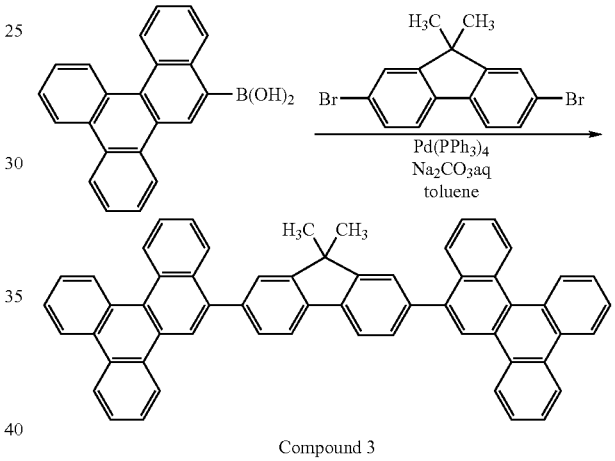

Compound 3

A compound was synthesized in the same manner as in the synthesis of the compound 1, except that 2,7-dibromo-9,9-dimethylfluorene which had been prepared by a known method was used instead of 1,4-dibromobenzene. As a result of mass spectroscopy, the resulting compound was confirmed to be an intended product. This intended product had an m/z value of 746 with respect to a molecular weight of 746.30.

Example 4

The following compound 4 was synthesized by the following reaction.

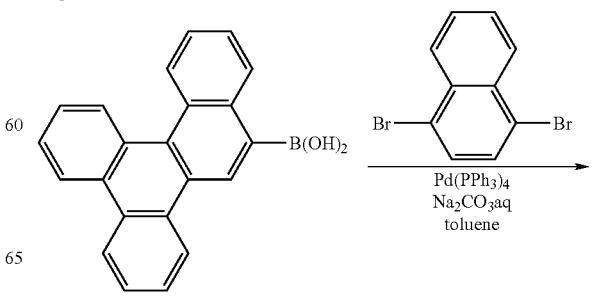

-continued

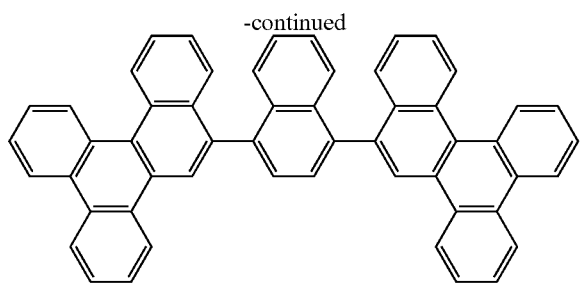

Compound 4

A compound was synthesized in the same manner as in the synthesis of the compound 1, except that 1,4-dibromonaphthalene was used instead of 1,4-dibromobenzene. As a result of mass spectroscopy, the resulting compound was confirmed to be an intended product. This intended product had an m/z value of 680 with respect to a molecular weight of 680.25.

Example 5

The following compound 5 was synthesized by the following reaction.

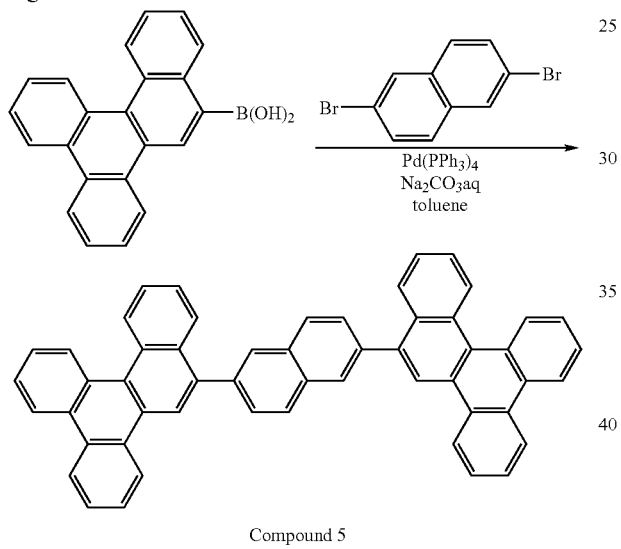

Compound 5

A compound was synthesized in the same manner as in the synthesis of the compound 1, except that 2,6-dibromonaphthalene was used instead of 1,4-dibromobenzene. As a result of mass spectroscopy, the resulting compound was confirmed to be an intended product. This intended product had an m/z value of 680 with respect to a molecular weight of 680.25.

Fabrication of Organic EL Device

Example 6

A glass substrate of 25 mm by 75 mm by 1.1 mm thick with an ITO transparent electrode (anode) (GEOMATEC CO., LTD.) was subjected to ultrasonic cleaning with isopropyl alcohol for 5 minutes, and cleaned with ultraviolet rays and ozone for 30 minutes. The cleaned glass substrate having the transparent electrode lines was mounted in a substrate holder of an apparatus for vacuum deposition. First, a 60 nm-thick film of the following compound A-1 was formed on the surface where the transparent electrode lines were formed so as to cover the transparent electrodes. Subsequent to the formation of the A-1 film, a 20 nm-thick film of the following compound A-2 was formed on this A-1 film.

Further, the compound 1 of the invention and a styryl amine derivative D-1 was deposited on this A-2 film in a thickness of 40 nm such that the film thickness ratio became 40:2. This film functioned as a blue-emitting layer.

The following compound (Alq) was deposited on this film to form a 20 nm-thick film as an electron-transporting layer. The film serves as an electron-injecting layer. Thereafter, LiF was formed into a film with a thickness of 1 nm. On this LiF film, metal Al was deposited in a thickness of 150 nm to form a metal cathode, whereby an organic EL device was fabricated.

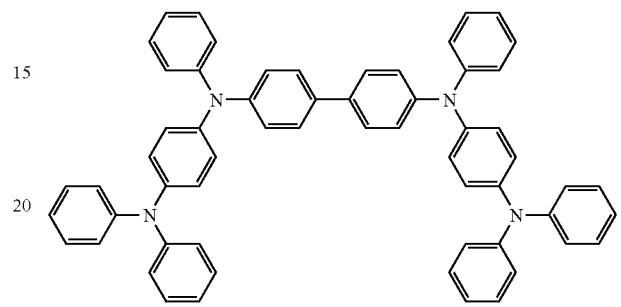

A-1

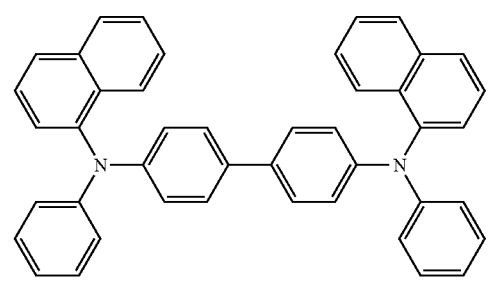

A-2

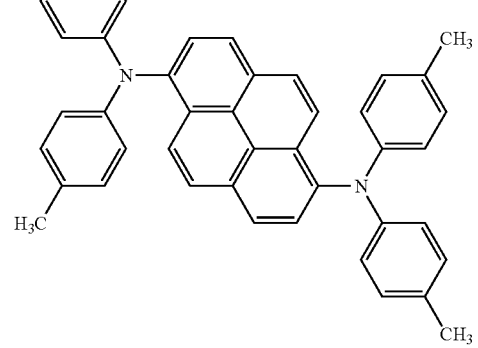

D-1

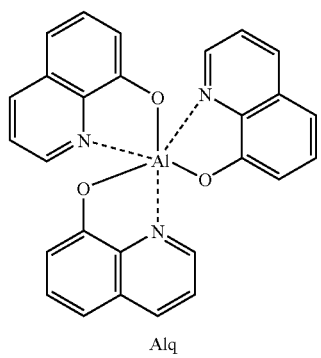

Alq

Examples 7 to 10

Organic EL devices were fabricated in the same manner as in Example 6, except that the compounds 2-5 shown in Table 1 were used instead of the compound 1.

Comparative Example 1

An organic EL device was fabricated in the same manner as in Example 6, except that the following compound B was used instead of the compound 1.

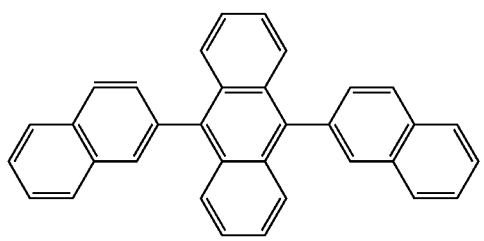

(B)

For the organic EL device fabricated in each Example above, the device performance when driven at a current density of 10 mA/cm² and the half life relative to the initial luminance of 1000 cd/m² were measured. The results are shown in Table 1.

Meanwhile, the luminous efficiency was measured by a method in which a prescribed voltage was applied to the device, and a current value at that time was measured, and at the same time, an emission luminance value was measured by means of a luminance meter (CS-1000, a spectroradiometer manufactured by Konica Minolta Holdings, Inc.).

TABLE 1

|  | Host | Dopant | Voltage (V) | Luminous efficiency (cd/A) | Emission color | Life (hour) |
|---|---|---|---|---|---|---|
| Example 6 | Compound 1 | D-1 | 6.5 | 6.5 | Blue | 6000 |
| Example 7 | Compound 2 | D-1 | 6.6 | 6.5 | Blue | 7000 |
| Example 8 | Compound 3 | D-1 | 6.5 | 6.3 | Blue | 5500 |
| Example 9 | Compound 4 | D-1 | 6.7 | 6.7 | Blue | 8000 |
| Example 10 | Compound 5 | D-1 | 6.7 | 6.7 | Blue | 8000 |
| Com. Ex. 1 | Compound B | D-1 | 7.0 | 6.0 | Blue | 4000 |

Example 11

A glass substrate of 25 mm by 75 mm by 1.1 mm thick with an ITO transparent electrode (GEOMATEC CO., LTD.) was subjected to ultrasonic cleaning with isopropyl alcohol for 5 minutes, and cleaned with ultraviolet rays and ozone for 30 minutes. The cleaned glass substrate with transparent electrode lines was mounted in a substrate holder of a vacuum vapor deposition apparatus.

First, a 50 nm-thick film of 4,4'-bis[N-(1-naphthyl)-N-phenenylamino]biphenyl (hereinafter abbreviated as the "NPD film") was formed by resistance heating deposition on the surface where the transparent electrode lines were formed so as to cover the transparent electrode. This NPD film functioned as a hole-injecting/transporting layer.

Next, on the NPD film, the compound 1 was formed into a film of 40 nm by resistance heating deposition. Simultaneously, as the phosphorescent dopant, the following PQIr (acac) was deposited such that the content thereof became 5 mass % of the entire emitted layer. This film functioned as a phosphorescent emitting layer.

On this phosphorescent emitting layer, the following compound I was formed into a film with a thickness of 10 nm by resistance heating deposition. The film of this compound I functioned as a hole-blocking layer.

On this film, tris(8-quinolinol)aluminum (Alq₃) complex was formed into a thickness of 30 nm. This film functioned as an electron-transporting layer.

Then, Li as a reductive dopant (Li source: manufactured by SAES Getters Co., Ltd.) and Alq were co-deposited, whereby an Alq:Li film (film thickness: 0.5 nm) was formed as an electron-injecting layer.

Metal aluminum was deposited on the Alq:Li film to form a metallic cathode (film thickness: 150 nm), whereby an organic EL device was fabricated.

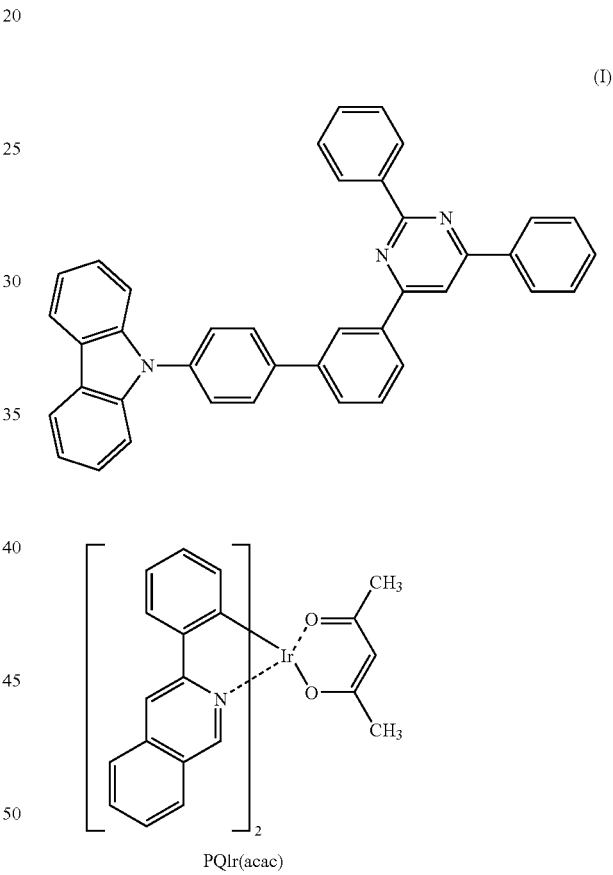

PQIr(acac)

Examples 12 to 15

Organic EL devices were fabricated in the same manner as in Example 11, except that the compounds 2 to 5 shown in Table 2 were used instead of the compound 1.

Comparative Example 2

An organic EL device was fabricated in the same manner as in Example 11, except that the following compound C was used instead of the compound 1.

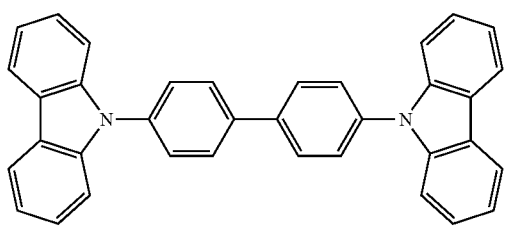

(C)

For the organic EL devices fabricated in Examples 11 to 15 and Comparative Example 2, the device performance when driven at a current density of 10 mA/cm² and the half life relative to the initial luminance of 1000 cd/m² were measured. The results are shown in Table 2.

Meanwhile, EQE (external quantum efficiency) can be obtained from the number of photons which can be calculated from an emission spectrum and the current density at the time of driving.

TABLE 2

| | Host | Dopant | Device performance EQE (%) | Life (Hour) |
|---|---|---|---|---|
| Example 11 | Compound 1 | PQIr(acac) | 18.3 | 30000 |
| Example 12 | Compound 2 | PQIr(acac) | 18.4 | 30000 |
| Example 13 | Compound 3 | PQIr(acac) | 18.4 | 25000 |
| Example 14 | Compound 4 | PQIr(acac) | 18.3 | 30000 |
| Example 15 | Compound 5 | PQIr(acac) | 18.3 | 30000 |
| Com. Ex. 2 | Compound C | PQIr(acac) | 18.2 | 3000 |

Example 16

The following compound 6 was synthesized by the following reaction.

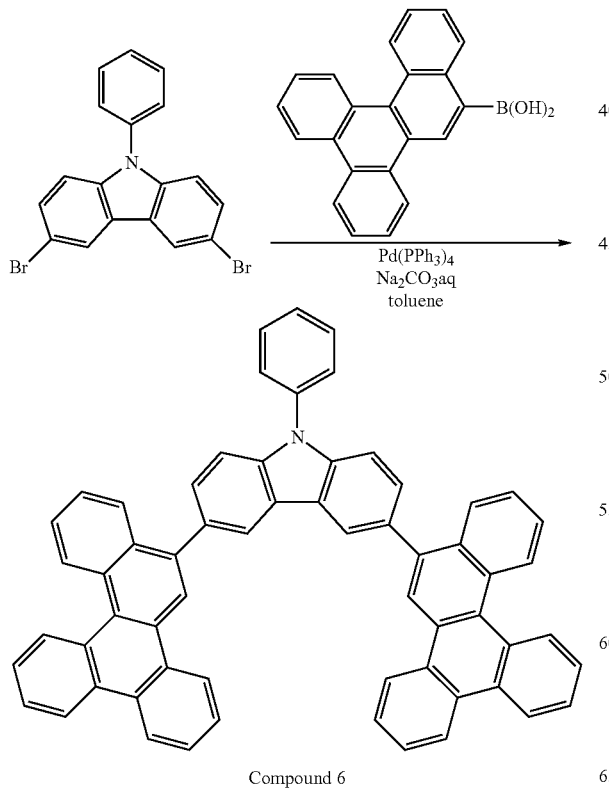

Compound 6

A compound was synthesized in the same manner as in the synthesis of the compound 1 (Example 1), except that N-phenyl-3,6-dibromocarbazole was used instead of 1,4-dibromobenzene. As a result of mass spectroscopy, the resulting compound was confirmed to be an intended product. This intended product had an m/z value of 795 with respect to a molecular weight of 795.29.

Example 17

The following compound 7 was synthesized by the following reaction.

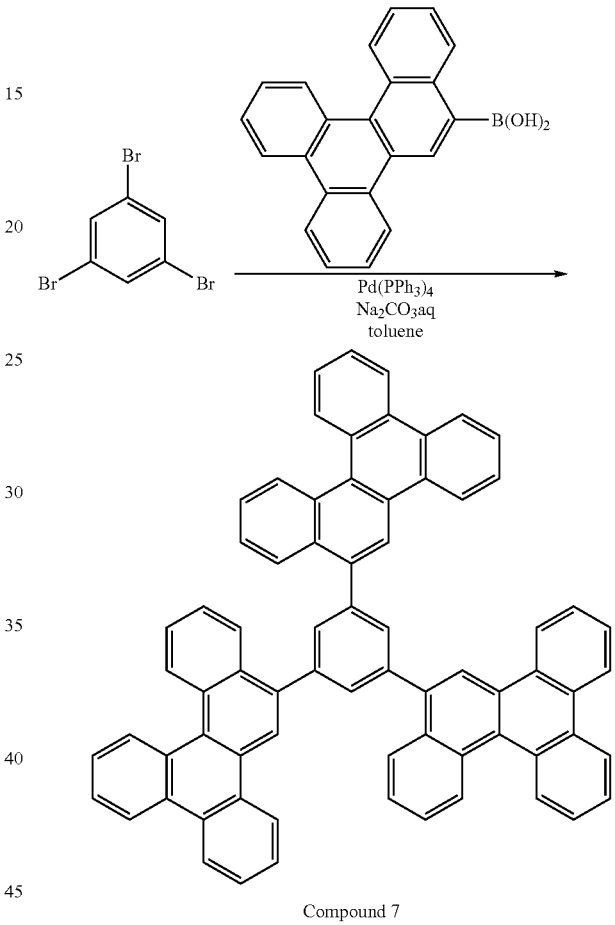

Compound 7

Under an argon atmosphere, 11.6 g of the benzo[g]chrysene-10-boronic acid, 2.36 g of 1,4-dibromobenzene, 0.693 g of tetraxis(triphenylphosphine)palladium(0), 120 mL of toluene and 60 mL of a 2M aqueous solution of sodium carbonate were placed in a flask. The resultant was refluxed with stirring for 8 hours. After cooling to room temperature, the reaction solution was extracted with toluene. An aqueous phase was removed, and an organic phase was washed with water and then with saturated brine, and dried with magnesium sulfate. After the magnesium sulfate was filtered out, the organic phase was concentrated. The residue was purified by a silica gel column chromatography, whereby 5.54 g of white crystals were obtained. As a result of mass spectrometry, the resulting crystals were confirmed to be an intended product. The intended product had an m/z value of 906 with respect to a molecular weight of 906.33.

Example 18

The following compound 8 was synthesized by the following reaction.

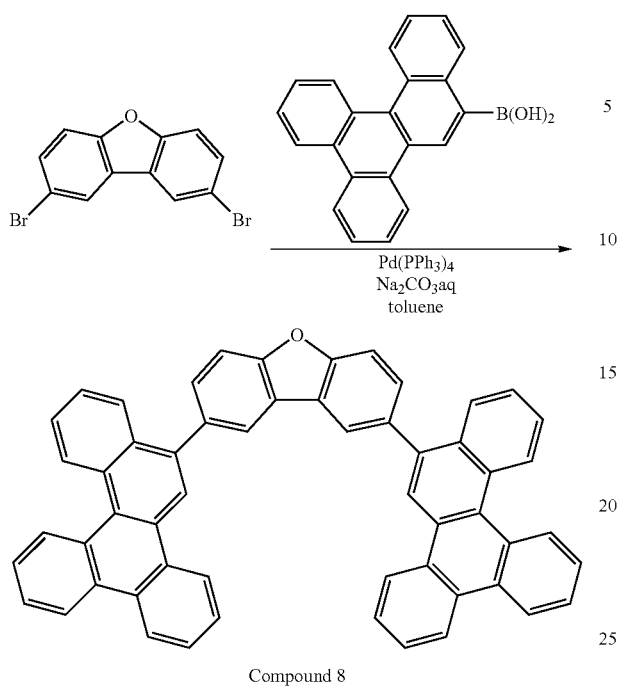

Compound 8

A compound was synthesized in the same manner as in the synthesis of the compound 1 (Example 1), except that 1,8-dibromobenzofuran was used instead of 1,4-dibromobenzene. As a result of mass spectroscopy, the resulting compound was confirmed to be an intended product. This intended product had an m/z value of 720 with respect to a molecular weight of 720.25.

Examples 19 to 21

Organic EL devices were fabricated in the same manner as in Example 11, except that the compounds 6 to 8 which had been prepared in Examples 16 to 18, which are shown in Table 3, were used instead of the compound 1. For the organic EL devices fabricated in Examples 19 to 21, the device performance when driven at a current density of 10 mA/cm$^2$ and the half life relative to the initial luminance of 1000 cd/m$^2$ were measured. The results are shown in Table 3.

Meanwhile, EQE (external quantum efficiency) can be obtained from the number of photons which can be calculated from an emission spectrum and the current density at the time of driving.

TABLE 3

| | Host | Dopant | Device performance EQE (%) | Life (Hour) |
|---|---|---|---|---|
| Example 19 | Compound 6 | PQIr(acac) | 18.0 | 20000 |
| Example 20 | Compound 7 | PQIr(acac) | 18.2 | 25000 |
| Example 21 | Compound 8 | PQIr(acac) | 18.4 | 26000 |

Industrial Applicability

The fused aromatic ring derivative of the invention is preferable as a material for an organic EL device, in particular, as an emitting material.

The organic EL device of the invention can be suitably used as a light source such as a planar emitting body and backlight of a display, a display part of a portable phone, a PDA, a car navigator, or an instrument panel of an automobile, an illuminator, and the like.

The documents described in the specification are incorporated herein by reference in its entirety.

The invention claimed is:

1. A fused aromatic ring derivative shown by the following formula (1):

(1)

wherein $R_a$ and $R_b$ are independently a hydrogen atom or a substituent, m and n are independently an integer of 1 to 13, and when m and n are two or more, $R_a$s and $R_b$s may be independently the same or different, and $L_1$ is a single bond or a substituted or unsubstituted divalent linking group, provided that the fused aromatic ring derivative shown by the formula (1) does not have an anthracene ring.

2. The fused aromatic ring derivative according to claim 1 shown by the following formula (2):

(2)

wherein $R_a$ and $R_b$ are independently a hydrogen atom or a substituent, m and n are independently an integer of 1 to 13, and when m and n are two or more, $R_a$s and $R_b$s may be independently the same or different, and $L_2$ is a single bond or a substituted or unsubstituted divalent linking group, provided that the fused aromatic ring derivative shown in the formula (2) does not have an anthracene ring.

3. The fused aromatic ring derivative according to claim 1, wherein $L_1$ or $L_2$ is a substituted or unsubstituted arylene group having 6 to 50 ring carbon atoms.

4. A material for an organic electroluminescence device comprising the fused aromatic ring derivative according to claim 1.

5. The material for an organic electroluminescence device according to claim 4, which is an emitting material.

6. An organic electroluminescence device comprising:
an anode, a cathode, and
one or more organic thin film layers comprising an emitting later between the anode and the cathode, wherein at least one of the organic thin film layers comprises the compound according to claim 1.

7. The organic electroluminescence device according to claim 6, wherein the emitting layer comprises the fused aromatic ring derivative.

8. The organic electroluminescence device according to claim 7, wherein the emitting layer comprises the fused aromatic ring derivative as a host material.

9. The organic electroluminescence device according to claim 6, wherein the emitting layer further comprises at least one of a fluorescent dopant and a phosphorescent dopant.

10. The organic electroluminescence device according to claim 9, wherein the fluorescent dopent is an arylamine compound.

11. The organic electroluminescence device according to claim 9, wherein the fluorescent dopant is a styrylamine compound.

12. The organic electroluminescence device according to claim 9, wherein the phosphorescent dopant is a metal complex compound.

* * * * *